United States Patent
Oryan (Orian) et al.

(10) Patent No.: US 11,407,827 B2
(45) Date of Patent: Aug. 9, 2022

(54) PROGNOSTIC BIOMARKER IN CANCER

(71) Applicant: TECHNION RESEARCH & DEVELOPMENT FOUNDATION LIMITED, Haifa (IL)

(72) Inventors: Amir Oryan (Orian), Haifa (IL); Yaniv Zohar, Haifa (IL); Emily Hersh-Avitan, Tiberias (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 136 days.

(21) Appl. No.: 16/980,600

(22) PCT Filed: Mar. 14, 2019

(86) PCT No.: PCT/IL2019/050287
§ 371 (c)(1),
(2) Date: Sep. 14, 2020

(87) PCT Pub. No.: WO2019/175881
PCT Pub. Date: Sep. 19, 2019

(65) Prior Publication Data
US 2021/0047400 A1 Feb. 18, 2021

Related U.S. Application Data

(60) Provisional application No. 62/642,907, filed on Mar. 14, 2018.

(51) Int. Cl.
*C07K 16/28* (2006.01)
*G01N 33/574* (2006.01)
*G01N 33/577* (2006.01)

(52) U.S. Cl.
CPC ........... *C07K 16/28* (2013.01); *G01N 33/574* (2013.01); *G01N 33/577* (2013.01); *C07K 2317/565* (2013.01)

(58) Field of Classification Search
CPC ................ C07K 16/18; C07K 2317/56; C07K 2317/565; G01N 33/574; G01N 33/577
See application file for complete search history.

(56) References Cited

U.S. PATENT DOCUMENTS 10,465,197 B2 * 11/2019 McClain ............... C07K 16/241
2011/0305687 A1 * 12/2011 Weng ....................... A61P 35/00
435/69.6

FOREIGN PATENT DOCUMENTS

WO 2010033371 A2 3/2010
WO 2016196328 A1 12/2016

OTHER PUBLICATIONS

Galili, N., Nayak, S., Epstein, J.A. and Buck, C.A. (2000), Rnf4, a RING protein expressed in the developing nervous and reproductive systems, interacts with Gscl, a gene within the DiGeorge critical region. Dev. Dyn., 218: 102-111; DOI: 10.1002/(SICI)1097-0177(200005)218:1<102::AID-DVDY9>3.0.CO;2-A.
Salonen J, Butzow R, Palvimo JJ, Heikinheimo M, Heikinheimo O. Oestrogen receptors and small nuclear ring finger protein 4 (RNF4) in malignant ovarian germ cell tumours. Mol Cell Endocrinol. Aug. 13, 2009;307(1-2):205-10. DOI: 10.1016/j.mce.2009.03.015.
Thomas JJ, Abed M, Heuberger J, Novak R, Zohar Y, Beltran Lopez AP, Trausch-Azar JS, Ilagan MXG, Benhamou D, Dittmar G, Kopan R, Birchmeier W, Schwartz AL, Orian A. RNF4-Dependent Oncogene Activation by Protein Stabilization. Cell Rep. Sep. 20, 2016;16(12):3388-3400. doi:10.1016/j.celrep.2016.08.024.
Diefenbacher, M., & Orian, A. (2016) Stabilization of nuclear oncoproteins by RNF4 and the ubiquitin system in cancer. Molecular & cellular oncology, 4(1), e1260671. DOI: 10.1080/23723556.2016.1260671.
Taishi Moriyama et al: "SUMO-modification and elimination of the active DNA demethylation enzyme TDG in cultured human cells", Biochemical and Biophysical Research Communications, 447, (2014), 419-424.
Masayuki Saito et al: "The SUMO-targeted ubiquitin ligase RNF4 localizes to etoposide-exposed mitotic chromosomes: Implication for a novel DNA damage response during mitosis", Biochemical and Biophysical Research Communications, 447, (2014), 83-88. http://dx.doi.org/10.1016/j.bbrc.2014.03.106.
Stefanie Koidl et al: "The SUMO2/3 specific E3 ligase ZNF451-1 regulates PML stability", Int J Biochem Cell Biol, Oct. 2016, 79, 478-487. https://doi.org/10.1016/j.biocel.2016.06.011.
PCT International Search Report for International Application No. PCT/IL2019/050287, dated Jun. 19, 2019, 5pp.
PCT Written Opinion for International Application No. PCT/IL2019/050287, completed Jun. 19, 2019, 7pp.
PCT International Preliminary Report on Patentability for International Application No. PCT/IL2019/050287, dated Sep. 15, 2020, 8pp.

* cited by examiner

*Primary Examiner* — Kimberly Ballard
(74) *Attorney, Agent, or Firm* — The Roy Gross Law Firm, LLC; Roy Gross

(57) ABSTRACT

The present invention is directed to a monoclonal antibody or an antigen-binding portion thereof having specific binding affinity to RING finger protein 4 (RNF4). The invention is further directed to use of the antibody or an antigen-binding portion thereof in detecting a RNF4-associated disease in a subject, such as cancer.

19 Claims, 5 Drawing Sheets
Specification includes a Sequence Listing.

PROGNOSTIC BIOMARKER IN CANCER

CROSS REFERENCE TO RELATED APPLICATIONS

This application is a National Phase of PCT Patent Application No. PCT/IL2019/050287 having International filing date of Mar. 14, 2019, which claims the benefit of priority of U.S. Provisional Patent Application No. 62/642,907, filed Mar. 14, 2018, the contents of which are incorporated herein by reference in their entirety.

FIELD OF INVENTION

The present invention is in the field of cancer prognosis.

BACKGROUND OF THE INVENTION

Cancer is intimately linked to dysregulated proteolysis. Mutations of oncoproteins' phosphorylation sites, which are identified frequently in cancer patients, are sufficient to impair degradation, and therefore promote tumorigenesis in a mouse model. Collectively, deregulated and increased oncoprotein stabilization and abundance is at the heart of tumorigenesis. In many cases, destabilizing phosphorylation is preceded by priming phosphorylation that initially potentiates the activity of oncogenes by less well-understood mechanisms. RING finger protein 4 (RNF4) belongs to a small group of RING ubiquitin ligases termed SUMO-Targeted Ubiquitin ligases (STUbL). In many cases, ubiquitylation by RNF4 leads to proteasomal degradation of SUMOylated proteins. Recent findings show that in the case of epithelial cancers and osteosarcoma, phosphorylation-dependent and RNF4-mediated ubiquitylation potentiates tumorigenic properties of cancer cells by stabilizing a subset of oncoproteins. While RNF4 is non-oncogenic on its own, it has been shown that it is essential for cancer cells to cope with oncogenic stress. Genes, such as RNF4 that are collectively termed "Non-Oncogenic Addiction" genes (NOA), are viewed as the "Achilles' heel" of tumors, and thus are potentially excellent targets for personalized therapy.

SUMMARY OF THE INVENTION

The present invention is directed to a monoclonal antibody or antigen-binding portion thereof having increased binding affinity to RING finger protein 4 (RNF4). The present invention is further directed to compositions, kits and methods, such as for the use of the antibody or antigen-binding portion thereof in the detection and diagnosis of RNA4-associated diseases, such as cancer.

According to one aspect there is provided an antibody or an antigen-binding portion thereof, the antibody comprising three light chain CDRs ($V_L$CDR) and three heavy chain CDRs ($V_H$CDR), wherein:

$V_{L1}$ CDR comprises the amino acid sequence as set forth in SEQ ID NO: 1 (SASSSVSYMY), $V_{L2}$ CDR comprises the amino acid sequence as set forth in SEQ ID NO: 2 (LTSNLAS), $V_{L3}$ CDR comprises the amino acid sequence as set forth in SEQ ID NO: 3 (QQWSSNPYM), $V_{H1}$ CDR comprises the amino acid sequence as set forth in SEQ ID NO: 4 (SYVMH), $V_{H2}$ CDR comprises the amino acid sequence as set forth in SEQ ID NO: 5 (YINPNNDGTKYNEKFKG), and $V_{H3}$ CDR comprises the amino acid sequence as set forth in SEQ ID NO: 6 (RVGHY).

In some embodiments, the antibody or an antigen-binding portion thereof comprises a variable region light chain comprising the amino acid sequence of SEQ ID NO: 7.

In some embodiments, the antibody or an antigen-binding portion thereof comprises a variable region heavy chain comprising the amino acid sequence of SEQ ID NO: 8.

In some embodiments, the antibody or an antigen-binding portion thereof comprises a constant region light chain comprising the amino acid sequence of SEQ ID NO: 9.

In some embodiments, the antibody or an antigen-binding portion thereof comprises a constant region heavy chain comprising the amino acid sequence of SEQ ID NO: 10.

In some embodiments, the antibody or an antigen-binding portion thereof comprises a light chain comprising the amino acid sequence of SEQ ID NO: 11.

In some embodiments, the antibody or an antigen-binding portion thereof comprises a heavy chain comprising the amino acid sequence of SEQ ID NO: 12.

In some embodiments, the antigen binding fragment is selected from the group consisting of a Fv, Fab, F(ab')$_2$, scFv or a scFv$_2$ fragment.

In some embodiments, the disclosed antibody or an antigen-binding portion thereof has specific binding affinity to RING finger protein 4 (RNF4).

In some embodiments, a composition comprising the disclosed antibody or an antigen-binding portion thereof and an acceptable carrier is provided.

According to another aspect, there is provided a method of detecting increased RNF4 levels in a sample compared to a baseline, comprising a step of contacting a sample with a first antibody, wherein the first antibody is the herein disclosed antibody or an antigen-binding portion thereof, and detecting increased binding between the RNF4 and the first antibody compared to the baseline, thereby detecting increased RNF4 levels in the sample.

In some embodiments, the method further comprises a step of contacting the sample with a second antibody or an antigen-binding portion thereof having specific binding affinity for phosphorylated translation initiation factor 2α (p-IF2α), and detecting increased binding between the p-IF2α and the second antibody in the sample compared to the baseline.

In some embodiments, the sample is derived from a subject.

In some embodiments, the increased binding between the RNF4 and the first antibody in the sample is indicative of the subject being afflicted with a RNF4-associated disease.

In some embodiments, the increased binding between the RNF4 and the first antibody in the sample is indicative of the subject having poor RNF4-associated disease prognosis.

In some embodiments, the increased binding between the p-IF2α and the second antibody in the sample compared to the baseline is indicative of: the subject being afflicted with a RNF4-associated disease, the subject having poor RNF4-associated disease prognosis, or both.

In some embodiments, the method further comprises a step of administering to the subject a therapeutically effective amount of an immune checkpoint inhibitor or a pharmaceutical composition comprising thereof.

In some embodiments, the immune checkpoint inhibitor is selected from the group consisting of: Pembrolizumab, Ipilimumab, Nivolumab, Atezolimumab, Avelumab, Durvalumab, and Cemiplimab.

In some embodiments, the RNF4-associated disease is cancer.

In some embodiments, the cancer is Estrogen Receptor α negative type of cancer (ER$_α$-negative).

According to another aspect, there is provided a kit for detecting increased RNF4 levels in a sample, comprising: a first antibody, wherein the first antibody is the herein disclosed antibody or an antigen-binding portion thereof; and a polynucleotide complementary to RNF4.

In some embodiments, the kit comprises instructions for: contacting the sample with the first antibody or an antigen-binding portion thereof, or with the polynucleotide complementary to RNF4; and detecting increased binding of the RNF4 with the antibody or with the complementary polynucleotide, compared to a baseline, thereby detecting increased RNF4 levels in the sample.

In some embodiments, the kit further comprises a second antibody or an antigen-binding portion thereof having specific binding affinity to p-IF2α.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
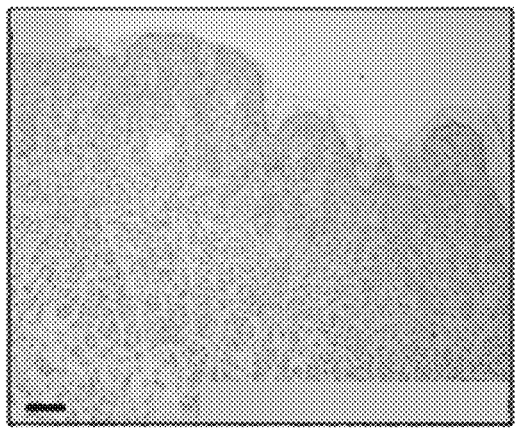
FIGS. 1A-1G are images and graphs describing the positive correlation between RNF4 increased levels and poor patient survival in melanoma. (1A-1B) are micrographs of Hematoxylin & Eosin (H&E) staining of patient-derived biopsies of nevi (1A) and melanoma (1B). (1C-1D) are micrographs of immunohistochemistry using an anti-RNF4 mAb, and regions shown in dashed square are shown in the insets. RNF4 is identified using the anti-RNF4 mAb (arrows) in melanoma biopsy (1D) but not in the nevi biopsy (1C). (1E) is a graph describing high level of RNF4 detected using anti-RNF4 mAb and melanoma tissue microarray correlated with overall shorter survival (n=29, p<0.001). (1F) is a graph describing high RNF4 protein level correlated with shorter disease-free survival (n=29, P<0.001). (1G) is a graph describing high RNF4 mRNA levels correlated with shorter overall survival (n=330, p<0.05).

The present invention provides monoclonal antibodies or antigen-binding portions thereof having increased binding affinity to RING finger protein 4 (RNF4). The present invention further provides compositions, kits and methods, such as for the use of the antibodies or antigen-binding portions thereof in the detection and diagnosis of RNF4-associated diseases, such as cancer.

In some embodiments, the present invention is directed to an antibody or an antigen-binding portions thereof having increased binding affinity to RNF4 (accession no. AAC52022.1).

In some embodiment, RNF4 has the amino acid sequence as set forth in SEQ ID NO: 25 (MSTRKRRGGAINSRQAQKRTREATSTPEISLEAEPIELVETAGDEIVDLTCESLEPV VVDLTHNDSVVIVDERRRPRRNARRLPQDHADSCVVSSDDEELSRDRDVYVTTH TPRNARDEGATGLRPSGTVSCPICMDGYSEIVQNGRLIVSTECGHVFCSQCLRDSL KNANTCPTCRKKINHKRYHPIYI).

As described herein, the anti-RNF4 antibodies of the invention can be used as a diagnostic and/or a prognosis agent for diseases or conditions wherein the RNF4 expression or activity is involved, such as cancer.

An "anti-RNF4 antibody", "an antibody which recognizes RNF4", or "an antibody against RNF4" is an antibody that binds to RNF4, with sufficient affinity and specificity. The term "antibody" as used herein encompasses "anti-RNF4 antibody", "an antibody which recognizes RNF4" and "an antibody against RNF4". In another embodiment, the term "antibody" encompasses an antigen-binding portion thereof.

As used herein, the terms "increased binding affinity" and "greater binding affinity" are interchangeable. In some embodiments, an antibody of the present invention has an increased binding affinity to RNF4. In one embodiment, increased affinity as used herein is by at least 10%, 30%, 50%, 75%, 100%, 150%, 250%, 500% or 1,000% compared to other epitopes, or any value and range therebetween. Each possibility represents a separate embodiment of the invention. In one embodiment, increased affinity as used herein is by 1-10%, 5-30%, 20-50%, 35-75%, 40-100%, 60-150%, 110-250%, 220-500% or 350-1,000% compared to other epitopes. In one embodiment, greater affinity as used herein is by at least 1.5-fold, 2-fold, 5-fold, 10-fold, 50-fold, 100-fold, 500-fold or 1,000-fold compared to other epitopes, or any value and range therebetween. Each possibility represents a separate embodiment of the invention.

The term "antibody" (also referred to as an "immunoglobulin") is used in the broadest sense and specifically encompasses polyclonal and monoclonal antibodies and antibody fragments so long as they exhibit the desired biological activity. In certain embodiments, the use of a chimeric antibody or a humanized antibody is also encompassed by the invention.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (www://imgt.cines.fr/) (IMGT®/V-Quest) to identify variable region segments, including CDRs. See, e.g., Brochet, X. et al, Nucl. Acids Res. J6:W503-508 (2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al, U.S. Dept. of Health and Human Services, "Sequence of Proteins of Immunological Interest" (1983).

TABLE 1

The amino acid sequences of the CDR sequences of the antibody of the invention.

| Region | mAb (SEQ ID NO) |
|---|---|
| $V_{L1}$ CDR | SASSSVSYMY (1) |
| $V_{L2}$ CDR | LTSNLAS (2) |
| $V_{L3}$ CDR | QQWSSNPYM (3) |
| $V_{H1}$ CDR | SYVMH (4) |
| $V_{H2}$ CDR | YINPNNDGTKYNEKFKG (5) |
| $V_{H3}$ CDR | RVGHY (6) |

An "antigen" is a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens.

The term "antigenic determinant" or "epitope" according to the invention refers to the region of an antigen molecule that specifically reacts with particular antibody. Peptide sequences derived from an epitope can be used, alone or in conjunction with a carrier moiety, applying methods known in the art, to immunize animals and to produce additional polyclonal or monoclonal antibodies.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No.

4,816,567; and Morrison et al, Proc. Natl. Acad. Sci. USA 57:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539). As used herein, the term "humanized antibody" refers to an antibody comprising a framework region from a human antibody and one or more CDRs from a non-human (usually a mouse or rat) immunoglobulin. Parts of a humanized immunoglobulin, except possibly the CDRs, are substantially identical to corresponding parts of natural human immunoglobulin sequences. In some cases, however, specific amino acid residues, for example in the framework regions, may be modified, so as to optimize performance of the humanized antibody. Importantly, the humanized antibody is expected to bind to the same antigen as the donor antibody that provides the CDRs. For further details, see e.g. U.S. Pat. No. 5,225,539 assigned to Medical Research Council, UK. The terms "a framework region from an acceptor human immunoglobulin" and "a framework region derived from an acceptor human immunoglobulin", and similar grammatical expressions are used interchangeably herein to refer to a framework region or portion thereof that has the same amino acid sequence of the acceptor human immunoglobulin.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed antibodies to be used in accordance with the methods provided herein may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are Natl. Acad. Sci. USA, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, neutralizing antibodies include: antibodies, fragments of antibodies, Fab and F(ab')2, single-domain antigen-binding recombinant fragments and natural nanobodies.

In some embodiments, the present invention provides nucleic acid sequences encoding the antibody of the present invention.

In one embodiment, an antibody as described herein comprises a light chain variable domain encoded by a DNA sequence comprising the following nucleic acid sequence (SEQ ID NO: 13): AGTGCCAGTTCAAGTGTAAGTTACATGTAC.

In one embodiment, an antibody as described herein comprises a light chain variable domain encoded by a DNA sequence comprising the following nucleic acid sequence (SEQ ID NO: 14): CTCACATCCAACCTGGCTTCT.

In one embodiment, an antibody as described herein comprises a light chain variable domain encoded by a DNA sequence comprising the following nucleic acid sequence (SEQ ID NO: 15): CAGCAGTGGAGTAGTAACCCGTACATG.

In one embodiment, an antibody as described herein comprises a light chain variable domain encoded by a DNA sequence comprising the following nucleic acid sequence (SEQ ID NO: 16):

```
ATGGATTTTCAAGTGCAGATTTTCAGCTTCCTGCTAATGAGTGCCTCAGT
CATAATGTCCAGGGGACAAATTGTTCTCACCCAGTCTCCAGCACTCATGT
CTGCATCTCCAGGGGAGAAGGTCACCATGACCTGCAGTGCCAGTTCAAGT
GTAAGTTACATGTACTGGTACCAGCAGAAGCCAAGATCTTCCCCCAAACC
CTGGATTTATCTCACATCCAACCTGGCTTCTGGAGTCCCTGCTCGCTTCA
GTGGCAGTGGGTCTGGGACCTCTTACTCTCTCACAATCAGCAGCATGGAG
GCTGAAGATGCTGCCACTTATTACTGCCAGCAGTGGAGTAGTAACCCGTA
CATGTTCGGAGGGGGGACCAAGCTGGAAATAAAA.
```

In one embodiment, an antibody as described herein comprises a heavy chain variable domain encoded by a DNA sequence comprising the following nucleic acid sequence (SEQ ID NO: 17): AGCTATGTTATGCAC.

In one embodiment, an antibody as described herein comprises a heavy chain variable domain encoded by a DNA sequence comprising the following nucleic acid sequence (SEQ ID NO: 18):

```
TATATTAATCCTAACAATGACGGTACTAAGTACAATGAGAAGTTCAAAGG
C.
```

In one embodiment, an antibody as described herein comprises a heavy chain variable domain encoded by a DNA sequence comprising the following nucleic acid sequence (SEQ ID NO: 19): CGGGTCGGGCACTAC.

In one embodiment, an antibody as described herein comprises a heavy chain variable domain encoded by a DNA sequence comprising the following nucleic acid sequence (SEQ ID NO: 20):

ATGGAATGGAGTTGGATATTTCTCTTTCTCCTGTCAGGAACTGCAGGTGT

CCACTCTGAGGTCCAGCTGCAGCAGTCTCGACCTGAGCTGGTAAAGCCTG

GGGCTTCAGTGAAGATGTCCTGCAAGGCTTCTGGATACACATTCACTAGC

TATGTTATGCACTGGGTGAAGCAGAAGCCTGGGCAGGGCCTTGAGTGGAT

TGGATATATTAATCCTAACAATGACGGTACTAAGTACAATGAGAAGTTCA

AAGGCAAGGCCACACTGACTTCAGACAAATCCTCCAGCACAGCCTATATG

GACCTCAGCAGCCTGACCTCTGAGGACTCTGCGGTCTATTACTGTGCAAG

CCGGGTCGGGCACTACTGGGGTCAAGGAACCTCAGTCACCGTCTCCTCA.

In one embodiment, an antibody as described herein comprises a light chain constant domain encoded by a DNA sequence comprising the following nucleic acid sequence (SEQ ID NO: 21):

CGGGCTGATGCTGCACCAACTGTATCCATCTTCCCACCATCCAGTGAGCA

GTTAACATCTGGAGGTGCCTCAGTCGTGTGCTTCTTGAACAACTTCTACC

CCAAAGACATCAATGTCAAGTGGAAGATTGATGGCAGTGAACGACAAAAT

GGCGTCCTGAACAGTTGGACTGATCAGGACAGCAAAGACAGCACCTACAG

CATGAGCAGCACCCTCACGTTGACCAAGGACGAGTATGAACGACATAACA

GCTATACCTGTGAGGCCACTCACAAGACATCAACTTCACCCATTGTCAAG

AGCTTCAACAGGAATGAGTGTTAG.

In one embodiment, an antibody as described herein comprises a heavy chain constant domain encoded by a DNA sequence comprising the following nucleic acid sequence (SEQ ID NO: 22):

GCCAAAACAACAGCCCCATCGGTCTATCCACTGGCCCCTGTGTGTGGAGA

TACAACTGGCTCCTCGGTGACTCTAGGATGCCTGGTCAAGGGTTATTTCC

CTGAGCCAGTGACCTTGACCTGGAACTCTGGATCCCTGTCCAGTGGTGTG

CACACCTTCCCAGCTGTCCTGCAGTCTGACCTCTACACCCTCAGCAGCTC

AGTGACTGTAACCTCGAGCACCTGGCCCAGCCAGTCCATCACCTGCAATG

TGGCCCACCCGGCAAGCAGCACCAAGGTGGACAAGAAAATTGAGCCCAGA

GGGCCCACAATCAAGCCCTGTCCTCCATGCAAATGCCCAGCACCTAACCT

CTTGGGTGGACCATCCGTCTTCATCTTCCCTCCAAAGATCAAGGATGTAC

TCATGATCTCCCTGAGCCCCATAGTCACATGTGTGGTGGTGGATGTGAGC

GAGGATGACCCAGATGTCCAGATCAGCTGGTTTGTGAACAACGTGGAAGT

ACACACAGCTCAGACACAAACCCATAGAGAGGATTACAACAGTACTCTCC

GGGTGGTCAGTGCCCTCCCCATCCAGCACCAGGACTGGATGAGTGGCAAG

GAGTTCAAATGCAAGGTCAACAACAAAGACCTCCCAGCGCCCATCGAGAG

AACCATCTCAAAACCCAAAGGGTCAGTAAGAGCTCCACAGGTATATGTCT

TGCCTCCACCAGAAGAAGAGATGACTAAGAAACAGGTCACTCTGACCTGC

ATGGTCACAGACTTCATGCCTGAAGACATTTACGTGGAGTGGACCAACAA

CGGGAAAACAGAGCTAAACTACAAGAACACTGAACCAGTCCTGGACTCTG

ATGGTTCTTACTTCATGTACAGCAAGCTGAGAGTGGAAAAGAAGAACTGG

GTGGAAAGAAATAGCTACTCCTGTTCAGTGGTCCACGAGGGTCTGCACAA

TCACCACACGACTAAGAGCTTCTCCCGGACTCCGGGTAAATGA.

In one embodiment, an antibody as described herein comprises a light chain encoded by a DNA sequence comprising the following nucleic acid sequence (SEQ ID NO: 23):

ATGGATTTTCAAGTGCAGATTTTCAGCTTCCTGCTAATGAGTGCCTCAGT

CATAATGTCCAGGGGACAAATTGTTCTCACCCAGTCTCCAGCACTCATGT

CTGCATCTCCAGGGGAGAAGGTCACCATGACCTGCAGTGCCAGTTCAAGT

GTAAGTTACATGTACTGGTACCAGCAGAAGCCAAGATCTTCCCCCAAACC

CTGGATTTATCTCACATCCAACCTGGCTTCTGGAGTCCCTGCTCGCTTCA

GTGGCAGTGGGTCTGGGACCTCTTACTCTCTCACAATCAGCAGCATGGAG

GCTGAAGATGCTGCCACTTATTACTGCCAGCAGTGGAGTAGTAACCCGTA

CATGTTCGGAGGGGGGACCAAGCTGGAAATAAAACGGGCTGATGCTGCAC

CAACTGTATCCATCTTCCCACCATCCAGTGAGCAGTTAACATCTGGAGGT

GCCTCAGTCGTGTGCTTCTTGAACAACTTCTACCCCAAAGACATCAATGT

CAAGTGGAAGATTGATGGCAGTGAACGACAAAATGGCGTCCTGAACAGTT

GGACTGATCAGGACAGCAAAGACAGCACCTACAGCATGAGCAGCACCCTC

ACGTTGACCAAGGACGAGTATGAACGACATAACAGCTATACCTGTGAGGC

CACTCACAAGACATCAACTTCACCCATTGTCAAGAGCTTCAACAGGAATG

AGTGTTAG.

In one embodiment, an antibody as described herein comprises a heavy chain encoded by a DNA sequence comprising the following nucleic acid sequence (SEQ ID NO: 24):

ATGGAATGGAGTTGGATATTTCTCTTTCTCCTGTCAGGAACTGCAGGTGT

CCACTCTGAGGTCCAGCTGCAGCAGTCTCGACCTGAGCTGGTAAAGCCTG

GGGCTTCAGTGAAGATGTCCTGCAAGGCTTCTGGATACACATTCACTAGC

TATGTTATGCACTGGGTGAAGCAGAAGCCTGGGCAGGGCCTTGAGTGGAT

TGGATATATTAATCCTAACAATGACGGTACTAAGTACAATGAGAAGTTCA

AAGGCAAGGCCACACTGACTTCAGACAAATCCTCCAGCACAGCCTATATG

GACCTCAGCAGCCTGACCTCTGAGGACTCTGCGGTCTATTACTGTGCAAG

CCGGGTCGGGCACTACTGGGGTCAAGGAACCTCAGTCACCGTCTCCTCAG

CCAAAACAACAGCCCCATCGGTCTATCCACTGGCCCCTGTGTGTGGAGAT

ACAACTGGCTCCTCGGTGACTCTAGGATGCCTGGTCAAGGGTTATTTCCC

TGAGCCAGTGACCTTGACCTGGAACTCTGGATCCCTGTCCAGTGGTGTGC

ACACCTTCCCAGCTGTCCTGCAGTCTGACCTCTACACCCTCAGCAGCTCA

GTGACTGTAACCTCGAGCACCTGGCCCAGCCAGTCCATCACCTGCAATGT

```
-continued
GGCCCACCCGGCAAGCAGCACCAAGGTGGACAAGAAAATTGAGCCCAGAG

GGCCCACAATCAAGCCCTGTCCTCCATGCAAATGCCCAGCACCTAACCTC

TTGGGTGGACCATCCGTCTTCATCTTCCCTCCAAAGATCAAGGATGTACT

CATGATCTCCCTGAGCCCCATAGTCACATGTGTGGTGGTGGATGTGAGCG

AGGATGACCCAGATGTCCAGATCAGCTGGTTTGTGAACAACGTGGAAGTA

CACACAGCTCAGACACAAACCCATAGAGAGGATTACAACAGTACTCTCCG

GGTGGTCAGTGCCCTCCCCATCCAGCACCAGGACTGGATGAGTGGCAAGG

AGTTCAAATGCAAGGTCAACAACAAAGACCTCCCAGCGCCCATCGAGAGA

ACCATCTCAAAACCCAAAGGGTCAGTAAGAGCTCCACAGGTATATGTCTT

GCCTCCACCAGAAGAAGAGATGACTAAGAAACAGGTCACTCTGACCTGCA

TGGTCACAGACTTCATGCCTGAAGACATTTACGTGGAGTGGACCAACAAC

GGGAAAACAGAGCTAAACTACAAGAACACTGAACCAGTCCTGGACTCTGA

TGGTTCTTACTTCATGTACAGCAAGCTGAGAGTGGAAAAGAAGAACTGGG

TGGAAAGAAATAGCTACTCCTGTTCAGTGGTCCACGAGGGTCTGCACAAT

CACCACACGACTAAGAGCTTCTCCCGGACTCCGGGTAAATGA.
```

In one embodiment, an antibody as described herein is encoded by a DNA molecule comprising a DNA sequence having at least 75% identity to a DNA sequence as described herein. In one embodiment, an antibody as described herein is encoded by a DNA molecule comprising a DNA sequence having at least 80% identity to a DNA sequence as described herein. In one embodiment, an antibody as described herein is encoded by a DNA molecule comprising a DNA sequence having at least 85% identity to a DNA sequence as described herein. In one embodiment, an antibody as described herein is encoded by a DNA molecule comprising a DNA sequence having at least 90% identity to a DNA sequence as described herein. In one embodiment, an antibody as described herein is encoded by a DNA molecule comprising a DNA sequence having at least 95% identity to a DNA sequence as described herein.

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding a polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use and being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the polynucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring".

Methods for Diagnosis and Prognosis

In some embodiments, the present invention is directed to methods of diagnosing or prognosing an RNF4-associated disease in a subject, comprising detecting increased RNF4 protein levels compared to a baseline in a sample derived from the subject, by contacting the sample with an anti-RNF4 antibody and detecting increased binding between the RNF4 and the antibody, wherein the increased binding between the RNF4 and the antibody in the sample is indicative of the subject having a RNF4-associated disease. In some embodiments, the present invention is directed to methods of diagnosing an RNF4-associated disease in a subject, comprising detecting increased RNF4 mRNA levels compared to a baseline in a sample derived from the subject, by contacting the sample with a RNF4 complementary polynucleotide(s) and detecting increased amount of RNF4 transcripts, wherein the increased amount of RNF4 transcripts in the sample is indicative of the subject having a RNF4-associated disease.

In some embodiments, the method of diagnosing an RNF4-associated disease in a subject, further comprises detecting increased phosphorylated e-IF2α (p-IF2α) levels compared to a baseline in a sample derived from the subject, by contacting the sample with an anti-p-IF2α and detecting increased binding between the p-IF2α and the anti-p-IF2α, wherein the increased binding between the p-IF2α and the anti-p-IF2α in the sample is indicative of a RNF4-associated disease in the subject.

In some embodiments, a subject diagnosed with an RNF4-associated disease is resistant to a therapeutic compound. In one embodiment, the therapeutic compound is a chemotherapeutic compound. In one embodiment, the therapeutic compound is a molecular therapeutic compound. In one embodiment, the therapeutic compound comprises a chemotherapeutic compound and a molecular therapeutic compound. In one embodiment, a subject having resistance to a therapeutic compound has poor prognosis. In one embodiment, poor prognosis is having a survival of 1%, 2%, 3%, 4%, 5%, 6%, 7%, 8%, 9%, 10%, 15% or 25% at most, or any value and range therebetween. Each possibility represents a separate embodiment of the invention. In one embodiment, poor prognosis is having a survival of 0.5-1%, 1-2%, 2-3%, 3-4%, 4-5%, 5-6%, 6-7%, 7-8%, 8-9% or 9-10% at most. Each possibility represents a separate embodiment of the invention. In some embodiments, a subject resistant to a therapeutic compound has increased levels of RNF4. In some embodiments, RNF4 levels of a subject resistant to a therapeutic compound are increased by at least 5%, 10%, 20%, 40%, 60% 80% or 100% compared to the baseline level of the subject, or any value and range therebetween. Each possibility represents a separate embodiment of the invention. As defined herein, the term "baseline level" refers to the level of RNF4 measured in the subject before or at early tumorigenesis. In another embodiment, an increased level of RNF4 in a subject is measured compared to a non-afflicted cell or tissue in the subject, such as adjacent tissue. In one embodiment, an increased level of RNF4 in a subject is measured compared to a non-afflicted control subject. In one embodiment, resistance to a therapeutic compound encompasses full desensitization and tolerance. In one embodiment, resistance is partial resistance. In one embodiment, partial resistance is at most 5%, 10%, 20%, 40%, 50%, 75%, 80% or 95%, or any value and range therebetween. Each possibility represents a separate embodiment of the invention. In some embodiments, a subject having partial resistance to a therapeutic compound has a lower prognosis compared to a subject having no resistance to a therapeutic compound. In some embodiments, a subject having partial resistance to a therapeutic compound has a greater prognosis compared to a fully resistant subject. In some embodiments, antibody of the present invention is used in a method for detecting increased levels of RNF4 in a subject having resistance for a therapeutic compound.

In some embodiments, a subject having increased levels of RNF4 has resistance to at least one therapeutic compound. In some embodiments, the therapeutic compound is an anti-cancer drug. In some embodiments, a subject having increased levels of RNF4 has resistance to one or more compounds selected from: a cytoskeletal drug, a kinase inhibitor, and a DNA replication inhibitor. In some embodiments, a cytoskeletal drug targets tubulin. In some embodiments, a cytoskeletal drug targeting tubulin, inhibits tubulin polymerization, inhibits tubulin depolymerization, or both. Types of anti-cancer drugs such as cytoskeletal drugs, kinase inhibitors, and DNA replication inhibitors, would be apparent to one of ordinary skill in the art. Non-limiting examples anti-cancer drug, include, but are not limited to Paclitaxel (i.e., cytoskeletal drug), Sorafenib (i.e., kinase inhibitor), and Carboplatin (DNA replication inhibitor). In some embodiments, a subject having increased levels of RNF4 has resistance to other therapeutic compounds known in the art.

By another aspect, the method of the invention further comprises a step of treating a subject having increased RNF4 levels.

In some embodiments, the method further comprises a step of administering to a subject being afflicted with a RNF4-associated disease a therapeutically effective amount of an immune checkpoint inhibitor or a pharmaceutical composition comprising thereof.

In some embodiments, the method further comprises a step of administering to a subject having poor RNF4-associated disease prognosis, a therapeutically effective amount of an immune checkpoint inhibitor or a pharmaceutical composition comprising thereof.

In some embodiments, the method further comprises a step of administering to either a subject being afflicted with a RNF4-associated disease or a subject having poor RNF4-associated disease prognosis, a therapeutically effective amount of an immune checkpoint inhibitor or a pharmaceutical composition comprising thereof.

As used herein, an "immune checkpoint inhibitor" refers to primarily cancer therapy harnessing specific antibodies to target immune checkpoints which include pivotal regulators known to be involved in activating or inhibiting pathways by which cancer cells or tumors evade the immune system. In one embodiment, the immune checkpoint inhibitor has specific binding affinity to CTLA4 (i.e., cytotoxic T-lymphocyte-associated protein 4). In one embodiment, the immune checkpoint inhibitor has specific binding affinity to PD-1 (i.e., protein death 1). In one embodiment, the immune checkpoint inhibitor has specific binding affinity to PD-L1 (i.e., PD-1 ligand 1). In some embodiments, the immune checkpoint inhibitor is selected from Pembrolizumab, Ipilimumab, Nivolumab, Atezolimumab, Avelumab, Durvalumab, and Cemiplimab.

As used herein the term "subject" refers to an individual, or a patient, which is a vertebrate, e.g., a mammal, including but not limited to, a human.

As defined herein "biological sample" refers to a physical specimen from any animal. In another embodiment, biological sample is obtained from a mammal. In another embodiment, biological sample is obtained from a human. In another embodiment, biological sample is obtained well within the capabilities of those skilled in the art. The biological sample includes, but not limited to, biological fluids such as serum, plasma, vitreous fluid, lymph fluid, synovial fluid, follicular fluid, seminal fluid, amniotic fluid, milk, whole blood, urine, cerebrospinal fluid, saliva, sputum, tears, perspiration, mucus, and tissue culture media, including tissue extracts such as homogenized tissue, and cellular extracts. In another embodiment, a biological sample is a biopsy. In another embodiment, a biological sample is a resected tumor. In another embodiment, a biological sample includes histological sections processed as known by one skilled in the art. The terms sample and biological sample are used herein interchangeably.

As used herein the term "disease" refers to any condition which would benefit from diagnosing with the antibody.

In some embodiments, methods of the present invention are directed to diagnosing a RNF4-associated disease. In some embodiments, a RNF4-associated disease comprises increased levels of RNF4 compared to a baseline level. In some embodiments, a RNF4-associated disease comprises increased levels of p-IF2α compared to a baseline level. In some embodiments, a RNF4-associated disease comprises increased levels of RNF4 and increased levels of p-IF2α compared to a baseline level. In some embodiments, increased levels comprise an increase of at least 5%, 10%, 20%, 40%, 50%, 65%, 80%, 90% or 99%, compared to a baseline, or any value and range therebetween. Each possibility represents a separate embodiment of the invention. In some embodiments, increased levels comprise an increase of 1-5%, 4-10%, 8-20%, 15-40%, 25-50%, 35-65%, 55-80%, 75-90% or 85-100%, compared to a baseline. Each possibility represents a separate embodiment of the invention. In some embodiments, increased levels comprise an increase of at least 2-fold, 5-fold, 10-fold, 20-fold, 40-fold, 50-fold, 80-fold, 90-fold or 100-fold, compared to a baseline, or any value and therebetween. Each possibility represents a separate embodiment of the invention.

In one embodiment, the present invention concerns a method for diagnosing, prognosticating or determining the suitability for treatment of a subject suffering from cancer.

As used herein, "cancer" or "pre-malignancy" are diseases associated with cell proliferation. Non-limiting types of cancer include carcinoma, sarcoma, lymphoma, leukemia, blastoma and germ cells tumors. In one embodiment, carcinoma refers to tumors derived from epithelial cells including but not limited to breast cancer, prostate cancer, lung cancer, pancreas cancer, and colon cancer. In one embodiment, sarcoma refers of tumors derived from mesenchymal cells including but not limited to sarcoma botryoides, chondrosarcoma, Ewing's sarcoma, malignant hemangioendothelioma, malignant schwannoma, osteosarcoma and soft tissue sarcomas. In one embodiment, lymphoma refers to tumors derived from hematopoietic cells that leave the bone marrow and tend to mature in the lymph nodes including but not limited to Hodgkin lymphoma, non-Hodgkin lymphoma, multiple myeloma and immunoproliferative diseases. In one embodiment, leukemia refers to tumors derived from hematopoietic cells that leave the bone marrow and tend to mature in the blood including but not limited to acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. In one embodiment, blastoma refers to tumors derived from immature precursor cells or embryonic tissue including but not limited to hepatoblastoma, medulloblastoma, nephroblastoma, neuroblastoma, pancreatoblastoma, pleuropulmonary blastoma, retinoblastoma and glioblastoma-multiforme. In one embodiment, germ cell tumors refer to tumors derived from germ cells including but not limited to germinomatous or seminomatous germ cell tumors (GGCT, SGCT) and nongerminomatous or nonseminomatous germ cell tumors (NGGCT, NSGCT). In one embodiment, germinomatous or seminomatous tumors include but not limited to germinoma, dysgerminoma and seminoma. In one embodiment, nongerminomatous or non-seminomatous tumors refers to pure and mixed germ cells tumors including but not limited to embryonal carcinoma, endodermal sinus tumor, choriocarcinoma, tearoom, polyembryoma, gonadoblastoma and teratocarcinoma.

In some embodiments, cancer is a neural cancer disease. Non-limiting types of neural cancer include acoustic neuroma, astrocytoma, chordoma, CNS lymphoma, craniopharyngioma, glioma, medulloblastoma, meningioma, metastatic brain tumor, primary brain lymphoma, spinal cord tumor, oligodendroglioma, pituitary tumor, primitive neuroectodermal tumor, Schwannoma, juvenile pilocytic astrocytoma, pineal tumor and rhabdoid tumor. In one embodiment, astrocytoma refers to tumor derived from astrocytes including but not limited to grade I—pilocytic astrocytoma, grade II—low-grade astrocytoma, grade III—anaplastic astrocytoma and grade IV—glioblastoma. In one embodiment, other types of glioma include but not limited to brain stem glioma, ependymoma, mixed glioma, optic nerve glioma and subependymoma.

In some embodiments, the present invention is directed to methods of prognosing a subject suffering from Estrogen Receptor negative (ER-negative) type of cancer. In one embodiment, ER is the alpha isoform of ER ($ER_\alpha$). In some embodiments, the present invention is directed to methods of prognosing a subject suffering from cancer, wherein cancer comprises any type of cancer excluding $ER_\alpha$-positive cancer). In some embodiments, the present invention is directed to methods of prognosing a subject suffering from $ER_\alpha$-negative cancer. In some embodiments, $ER_{60}$-negative cancer types comprise any cancer type excluding $ER_\alpha$-positive cancers. In one embodiment, $ER_\alpha$-positive cancer is selected from the group consisting of: breast cancer, ovarian cancer, endometrial cancer and prostate cancer.

In some embodiments, monoclonal antibodies of the present invention are useful for the diagnosis, detection and staging of a disease. In some embodiments, monoclonal antibodies of the present invention are useful for the diagnosis, detection, and staging of a human disease. In some embodiments, monoclonal antibodies of the present invention are useful for the diagnosis, detection and staging of cancer.

In some embodiments, polynucleotide(s) of the present invention are useful for the diagnosis, detection and staging of a disease. In some embodiments, polynucleotide(s) of the present invention are useful for the diagnosis, detection, and staging of a human disease. In some embodiments, polynucleotide(s) of the present invention are useful for the diagnosis, detection and staging of cancer. In some embodiments, cancer is ERα-negative type of cancer.

In one embodiment, the monoclonal antibodies and antigen-binding portion thereof of the present invention are humanized or fully human.

In some embodiment, the present invention provides a method of diagnosing a malignancy in a subject comprising administering to the subject a therapeutically effective amount of a therapeutic conjugate comprising the monoclonal antibodies of the present invention or fragment thereof or an antibody fusion protein or fragment thereof, wherein the monoclonal antibodies of the present invention or fragment thereof or antibody fusion protein or fragment thereof is bound to at least one diagnostic agent and then formulated in a suitable excipient.

The use of monoclonal antibodies for in-vitro diagnosis is well-known to one skilled in the art. For example, see Carlsson et al., Bio/Technology 7 (6): 567 (1989). For example, monoclonal antibodies can be used to detect the presence of a tumor-associated antigen in tissue from biopsy samples. Monoclonal antibodies also can be used to measure the amount of tumor-associated antigen in clinical fluid samples using techniques such as radioimmunoassay, enzyme-linked immunosorbent assay, and fluorescence immunoassay. Conjugates of tumor-targeted monoclonal antibodies and toxins can be used to selectively kill cancer cells in vivo (Spalding, Bio/Technology 9(8): 701 (1991); Goldenberg, Scientific American Science & Medicine 1(1): 64 (1994)). For example, therapeutic studies in experimental animal models have demonstrated the anti-tumor activity of antibodies carrying cytotoxic radionuclides.

Furthermore, the present invention includes methods of diagnosing cancer in a subject. In some embodiments, diagnosis is accomplished by administering a diagnostically effective amount of a diagnostic conjugate, formulated in a pharmaceutically suitable excipient, and detecting the label. The monoclonal antibodies of the present invention or derived fusion proteins or fragments thereof may be conjugated to the diagnostic/detection agent or be administered unconjugated to the diagnostic/detection agent, but before, concurrently, or after administration of the diagnostic/detection agent. In one embodiment, a suitable non-radioactive diagnostic/detection agent is a contrast agent suitable for magnetic resonance imaging (MRI), X-rays, computed tomography (CT) or ultrasound. In another embodiment, magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

In some embodiments, contrast agents, such as MRI contrast agents, contemplated in the present invention include, but not limited to, gadolinium ions, lanthanum ions, dysprosium ions, iron ions, manganese ions or other comparable label, CT contrast agents, and ultrasound contrast agents. In another embodiment, paramagnetic ions are suitable for the present invention. In one embodiment, paramagnetic ions include chromium3+, manganese2+, iron3+, iron2+, cobalt2+, nickel2+, copper2+, neodymium3+, samarium3+, ytterbium3+, gadolinium3+, vanadium2+, terbium3+, dysprosium3+, holmium3+ and erbium3+, with gadolinium being particularly preferred. In another embodiment, ions useful in other contexts, such as X-ray imaging, include but are not limited to lanthanum3+, gold3+, lead2+, and especially bismuth3+. In another embodiment, metals are also useful in diagnostic/detection agents, including those for magnetic resonance imaging techniques. In one embodiment, these metals include, but are not limited to: Gadolinium, manganese, iron, chromium, copper, cobalt, nickel, dysprosium, rhenium, europium, terbium, holmium and neodymium. In another embodiment, loading an antibody component with radioactive metals or paramagnetic ions may require reacting the antibody with a reagent having a long tail to which are attached a multiplicity of chelating groups for binding the ions. In one embodiment, such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

In some embodiments, conjugated diagnostic agents are radiopaque and contrast materials. In one embodiment these radiopaque diagnostic agents are used for enhancing X-rays and computed tomography, and include iodine compounds, barium compounds, gallium compounds, thallium compounds, etc. In another embodiment, specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

In some embodiments, the conjugated diagnostic agent is a fluorescent agent. In another embodiment, fluorescent labeling compounds include fluorescein isothiocyanate, rhodamine, phycoerytherin, renographin, phycocyanin, allophycocyanin, o-phthaldehyde and fluorescamine. In one embodiment, rhodamine and fluorescein are often linked via an isothiocyanate intermediate. In one embodiment, fluorescently-labeled antibodies are particularly used for flow cytometry analysis.

In some embodiments, the antibodies, fusion proteins, and fragments thereof of this invention can be detectably labeled by coupling the antibody to a chemiluminescent compound. In one embodiment, chemiluminescent labeling compounds include, but are not limited to, luminol, isoluminol, an aromatic acridinium ester, an imidazole, an acridinium salt and an oxalate ester, and others.

In some embodiments, a bioluminescent compound can be used to label the antibodies and fragments thereof the present invention. In one embodiment, bioluminescent labeling compounds include, but are not limited to luciferin, luciferase and aequorin.

Compositions

The present invention is also directed to compositions for human diagnostic use. In some embodiments, there is provides an antibody which recognizes RNF4, for the manufacture of a composition for the diagnosis of the conditions as described herein.

The molecules of the present invention may be dissolved, dispersed or admixed in an excipient that is acceptable and compatible with the ingredient of the invention as is well known in the art. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, and pH buffering agents.

In another embodiment, the compositions of the invention may be formulated in the form of an acceptable salt of the polypeptides of the present invention or their analogs, or derivatives thereof. In another embodiment, acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

As used herein, the term "carrier" refers to a diluent, adjuvant, excipient, or vehicle with which the compound is administered. Such carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the composition is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; and agents for the adjustment of tonicity such as sodium chloride or dextrose are also envisioned. The carrier may comprise, in total, from about 0.1% to about 99.99999% by weight of the pharmaceutical compositions presented herein.

In another embodiment, the compositions of the invention take the form of solutions, suspensions, emulsions, tablets, pills, capsules, powders, gels, creams, ointments, foams, pastes, sustained-release formulations and the like. In another embodiment, the compositions of the invention can be formulated as a suppository, with traditional binders and carriers such as triglycerides, microcrystalline cellulose, gum tragacanth or gelatin.

According to an embodiment of the invention, compositions contain 0.1%-95% of the antibody of the present invention, derivatives, or analogs thereof. According to another embodiment of the invention, compositions contain 1%-70% of the antibody derivatives, or analogs thereof. According to another embodiment of the invention, the composition or formulation may contain a quantity of antibody, derivatives, or analogs thereof.

The presently described antibody, derivatives, or analogs thereof may also be contained in artificially created structures such as liposomes, ISCOMS, slow-releasing particles, and other vehicles which increase the half-life of the peptides or polypeptides. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

Kit

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation.

In some embodiments, the kit comprises a probe molecule, an antibody molecule, or both. In some embodiments, the kit provides and enzyme and a substrate thereof.

In some embodiments, the kit further provides reagents and/or buffers, such as hybridization or binding buffer, for improving binding of the molecule to the microorganism biomarker. In some embodiments, the kit further provides reagents and/or buffers for detecting binding of the molecule to the microorganism biomarker. In some embodiments, the antibody is conjugated to a dye molecule. In some embodiments, the antibody is conjugated to an enzyme, non-limiting examples of which comprise alkaline phosphatase and horse radish peroxidase. In some embodiments, detection buffers comprises an enzyme's specific substrate. In some embodiments, the enzyme catalyzes a reaction on the substrate giving rise to a detectable product. In some embodiments, the product is soluble or insoluble. Non-limiting examples of substrates include, but are not limited to, CDP star, NPP, NBT-BCIP, and others, all which would be apparent to one of ordinary skill in the art.

According to some embodiments, the present invention is directed to a kit comprising a first antibody or an antigen-binding portion thereof. In some embodiments, the first antibody is the antibody of the invention or an antigen-binding portion thereof.

According to some embodiments, the present invention is directed to a kit comprising a polynucleotide complementary to RNF4 transcript. As used herein, the complementarity % of the complementary polynucleotide to the RNF4 transcript is at least 70%, 80%, 90%, 95%, or 100% complementary, or any value and range therebetween. Each possibility represents a separate embodiment of the invention. In some embodiments, the complementarity % of the complementary polynucleotide to the RNF4 transcript is 70-80%, 75-90%, 83-93%, 91-97%, or 95-100% complementarity. Each possibility represents a separate embodiment of the invention.

According to some embodiments, the kit further comprises a second antibody or an antigen-binding portion thereof. In some embodiments, the second antibody or an antigen-binding portion thereof has specific binding affinity to the phosphorylated translation initiation factor 2α (i.e., p-IF2α).

According to some embodiments, the kit comprises instructions for: (1) contacting a sample with: (i) the first antibody or (ii) the complementary polynucleotide, and (2) detecting increased levels of RNF4.

According to some embodiments, the kit comprises instructions for: (1) contacting a sample with: (i) the second antibody, and (2) detecting increased levels of p-IF2α.

In some embodiments, the components of the kit disclosed above are sterile. As used herein, the term "sterile" refers to a state of being free from biological contaminants. Any method of sterilization is applicable and would be apparent to one of ordinary skill in the art.

In some embodiments, the components of the kit are packaged within a container.

In some embodiments, the container is made of a material selected from the group consisting of thin-walled film or plastic (transparent or opaque), paperboard-based, foil, rigid plastic, metal (e.g., aluminum), glass, etc.

In some embodiments, the content of the kit is packaged, as described below, to allow for storage of the components until they are needed.

In some embodiments, some or all components of the kit may be packaged in suitable packaging to maintain sterility.

In some embodiments, the components of the kit are stored in separate containers within the main kit containment element e.g., box or analogous structure, may or may not be an airtight container, e.g., to further preserve the sterility of some or all of the components of the kit.

In some embodiments, the instructions may be recorded on a suitable recording medium or substrate. For example, the instructions may be printed on a substrate, such as paper or plastic, etc.

In some embodiments, the instructions may be present in the kit as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In other embodiments, the actual instructions are not present in the kit, but means for obtaining the instructions from a remote source, e.g. via the interne, are provided. An example of this embodiment is a kit that includes a web address where the instructions can be viewed and/or from which the instructions can be downloaded. As with the instructions, this means for obtaining the instructions is recorded on a suitable substrate.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); "Monoclonal Antibodies: Methods and Protocols". Vincent Ossipow, Nicolas Fischer. Humana Press (2014); "Monoclonal Antibodies: Methods and Protocols". Maher Albitar. Springer Science & Business Media (2007), all of which are incorporated by reference. Other general references are provided throughout this document.

MATERIALS AND METHODS

Antibodies

Antibody Sequencing and Used Antibodies

Total RNA was isolated from the hybridoma cells following the technical manual of TRIzol® Reagent. Total RNA was then reverse-transcribed into cDNA using either isotype-specific anti-sense primers or universal primers following the technical manual of PrimeScript™ 1$^{st}$ Strand cDNA Synthesis Kit. Antibody fragments of $V_H$, $V_L$, $C_H$ and $C_L$ were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned, and the consensus sequence was provided.

For the detection of p-eIF2α, α-human p-eIF2α (#3398, Cell Signaling Technology) was used.

Resistance to Vemurafenib in Cell Culture and In Vivo

Cells were infected with pINDUCER conditional doxycycline lentiviral vectors coding for control or RNF4 shRNA. shRNA was induced by the addition of Doxycycline (DOX) at a concentration of 0.5 μg/ml for 4 days in vitro and at a concentration of 2 mg/ml in drinking water for the in vivo experiment.

For the in vitro experiment A375R cells, infected with either shRNF4 or scrambled control, were plated in 96 wells plate at 1,000 cells/well. Cells were exposed to increasing concentrations of Vemurafenib for 6 days. Cell viability was measured using ATPLite assay.

For the in vivo experiment, $1 \times 10^6$ A375R cells were injected subcutaneously to six-week-old female nude mice. Three days after injection Dox was added to drinking water and the mice were treated with oral Vemurafenib. Briefly, Tumor growth was monitored twice per week for four weeks, at which point the mice were sacrificed and tumors were harvested.

Pathology Immunohistochemistry of Tumors and Patient Samples

Xenograft-derived tumors were fixed in formalin 5%, embedded in paraffin and then sectioned at 5 μm and immunostained with indicated antibodies. Slides were subjected to antigen retrieval using Dako Target Retrieval Solution and incubated for 1 hour with blocking solution (Dako). The blocked sections were incubated overnight at 4° C. with the indicated antibodies and diluted 1:200 in Dako Antibody Diluent. Slides were then washed thrice with PBS, incubated for 2 hours at 25° C. with relevant secondary antibody diluted 1:200 in Dako Antibody Diluent, washed again with PBS, revealed with Simple Stain AEC solution (Histofine), and counterstained with hematoxylin.

Human samples were obtained from the Institute of Pathology and dermatology, RAMBAM Health care campus, Haifa, Israel. Paraffin embedded sections prepared and immunostained with anti-RNF4 antibody using an automated Bench Mark XT system. Certified GI and dermopathologists confirmed diagnosis of each case. All experiments with human tissues were conducted under Helsinki committee approval committee approval number 0239-12-RMB.

Analysis of Melanoma Tissue Microarray (TMA)

Tissue microarrays were constructed as previously described (Jilaveanu et al. (2009)). Briefly, core needle biopsies of previously paraffin-embedded blocks were collected and mounted on the same slide. Tumors were stained using α-RNF4 mAb 8D10 antibody and assessed for RNF4 level. Clinical data regarding response to treatment, disease-free and overall survival were also collected and analyzed.

Statistical Analysis

Standard error of the mean (SEM), and t-test comparisons were performed using GraphPad Prism and ANOVAs software. In all experiments, significance was as follows: **=p<0.0001, *=P<0.001, **=P<0.05, *=P<0.01.

Example 1

High RNF4 Correlates with Poor Outcome in Melanoma

Figure 1B:
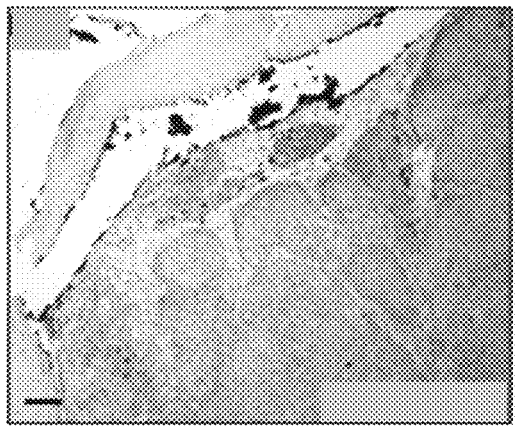
Figure 1C:
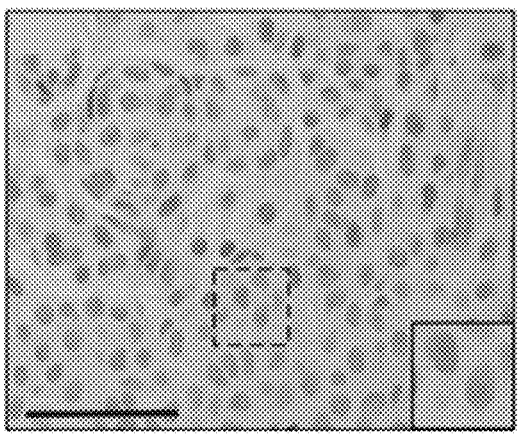
Figure 1D:
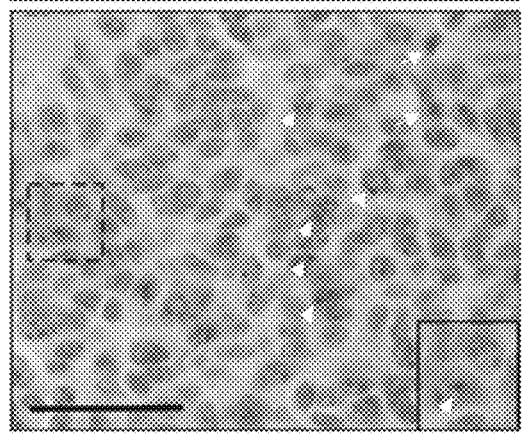
Figure 1E:
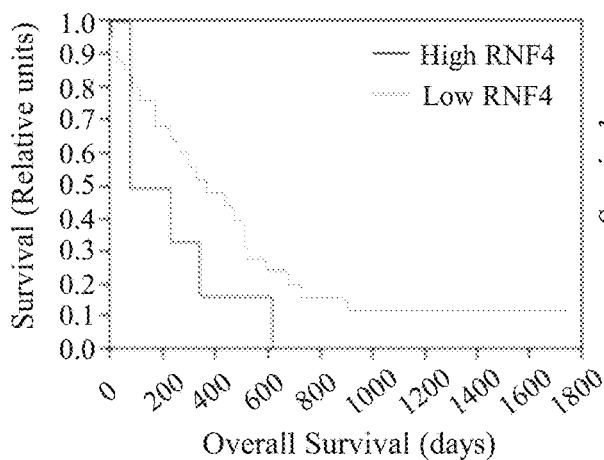
Figure 1F:
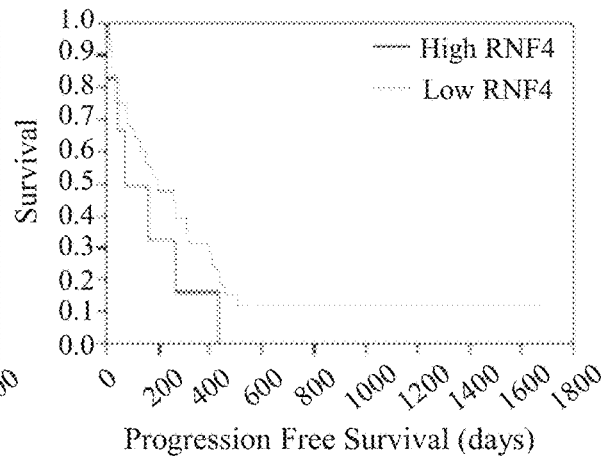

RNF4 protein were observed in 40% of patient-derived melanoma biopsies (4/10), but only in one nevi (1/10 benign lesion; FIGS. 1A and 1B; n=20). The overall survival was shorter in patients with biopsies exhibiting high RNF4 protein level (241±88 d, n=6), compared with patient-derived biopsies exhibiting low RNF4 level (412±60 d, n=22) (FIG. 1C). Furthermore, the inventors determined that high RNF4 protein level is associated with shorter period of disease free survival; 239±36 d in cases of low RNF4 (n=22), compared to 166±67 d in high RNF4 cases (n=6) (FIG. 1D).

Figure 1G:
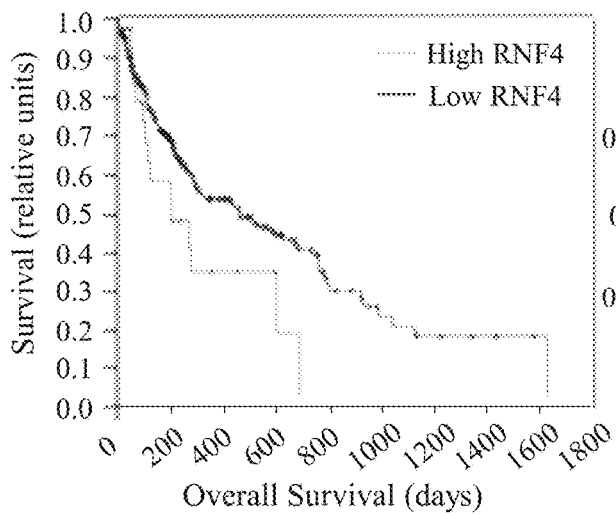

Screening patient-derived melanoma samples, the inventors found that progression-free survival was longer for patients whose melanomas expressed low RNF4 mRNA levels than patients with high RNF4 expression. The inventors also found that melanoma samples expressing high levels of RNF4 mRNA correlated with poorer overall survival (FIG. 1G. n=330, p<0.05).

By screening patient-derived melanoma samples, the inventors found that high RNF4 protein level further correlated with elevated protein levels of the phosphorylated translation intimation factor p-eIF2α. Moreover the inventors found that RNF4-depndent resistance to Vemurafenib also depends on p-eIF2α (FIG. 3).

Example 2

High RNF4 Expression Indicates Chemotherapy Non-Responsiveness

Figure 2A:
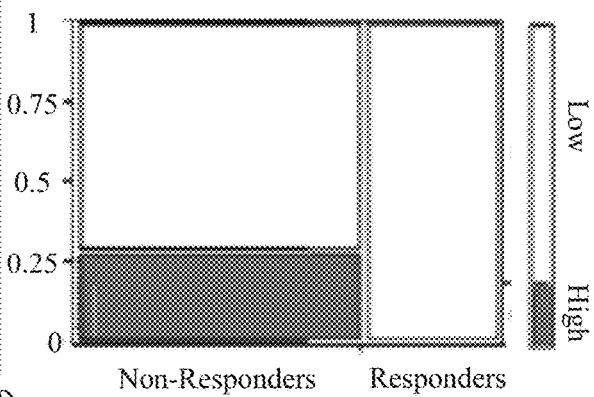
FIGS. 2A-2D are graphs describing the positive correlation between increased levels of RNF4 protein and resistance to targeted therapy. (2A) is a tissue microarray (TMA) analysis of responding and non-responding melanoma patients (n=31) using the anti-RNF4 antibody described herein. (2B) is a graph of cell viability assay; A375 cells resistance to Vemurafenib are sensitive to shRNF4 targeting but not control. (2C) is a graph describing that in the presence of Vemurafenib in a xenograft mouse model, tumors expressing shRNF4 tumors develop slower and are smaller than scRNA control expressing tumors. (2D) is a graph describing that expression of RNF4 in A375 cells induces resistance to PLX4032 (Vemurafenib). A375 human melanoma cells were infected with either control (GFP) or Dox-inducible RNF4-coding viruses. Cell viability was monitored after treatment with PLX4032 at the indicated concentrations for 96 hours. Three biological repeats are presented.
Figure 2B:
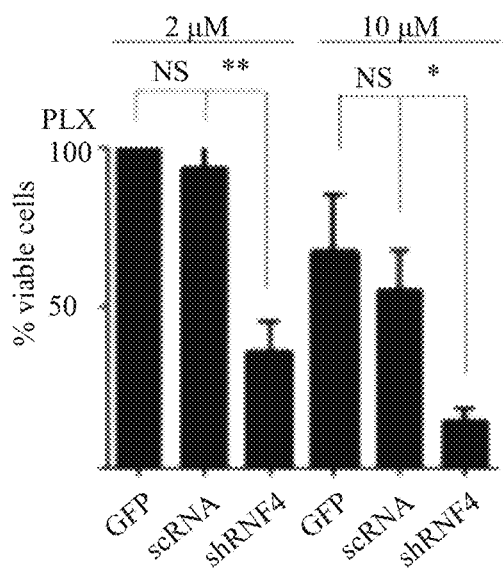
Figure 2C:
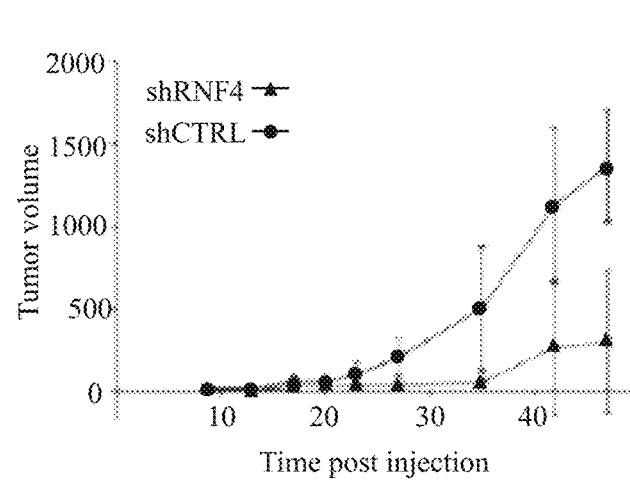
Figure 2D:
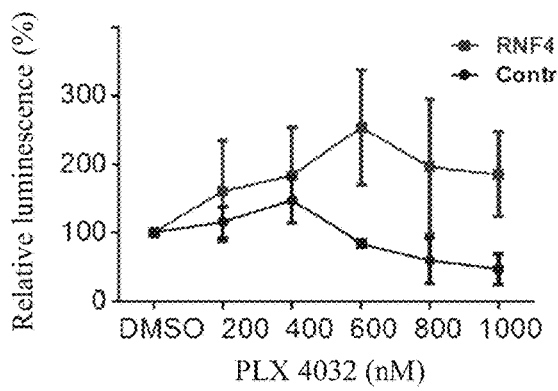
Figure 3A:
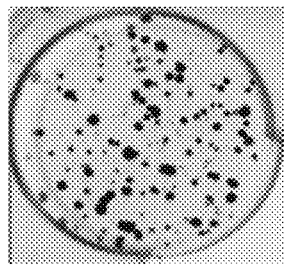
FIGS. 3A-3O are images and graphs showing that RNF4 activity in cancer depends on the phosphorylated form of translation initiation factor (i.e., p-eIF2a). (3A-3D) are micrographs of a colony formation experiment using of A375 cells infected with the following vectors: FLAG and scrambled RNA (scRNA) encoding vectors (3A); FLAG and short hairpin RNF4 (shRNF4) encoding vectors (3B); FLAG-eIF2α and scRNA encoding vectors (3C); and FLAG-eIF2α and shRNF4 encoding vectors (3D). Expression of eIF2α restored the ability of A375 to form foci that was compromised upon loss of RNF4. (3E) is a graph showing the quantification of foci formation of three independent biological repeats of FIGS. 3A-3D. (3F) is a graph showing quantification of p-eIF2α positive biopsies in low- and high-RNF4-expressing human melanoma biopsies, n=10, **** p<0.0001. (3G-3J) are representative micrographs of immunohistochemistry of RNF4 protein (3G-3H) and p-eIF2α (3I-3J) of patient samples quantified in FIG. 3F. In (3G-3J) dashed squares indicate magnified area; (staining was achieved using immunoperoxidase, magnification ×400). (3G-3H) Immunostaining of RNF4 protein of patient-derived melanoma biopsies using α-RNF4. (3I-3J) Immunostaining of p-eIF2α protein of patient-derived melanoma biopsies. (3G and 3I) are biopsies of low RNF expressing patients, and (3H and 3J) are biopsies of high RNF expressing patients. (3K-3N) are micrographs of a colony formation experiment using of A375 cells infected with the following vectors: FLAG and scrambled RNA (scRNA) encoding vectors (3K); FLAG and short hairpin RNF4 (shRNF4) encoding vectors (3L); FLAG-eIF2α and scRNA encoding vectors (3M); and FLAG-eIF2α and shRNF4 encoding vectors (3N). Overexpression of eIF2 in A375R cells subjected to RNF4 knockdown, partially restored resistance to PLX4032 (FIG. 3N). Expression of eIF2α restored the ability of A375 to form foci that was compromised upon loss of RNF4. (3O) is a graph showing the quantification of foci formation of three independent biological repeats of FIGS. 3K-3N.
Figure 3B:
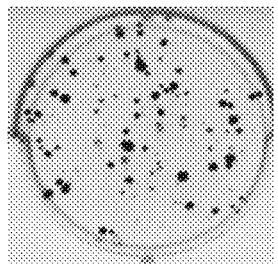
Figure 3C:
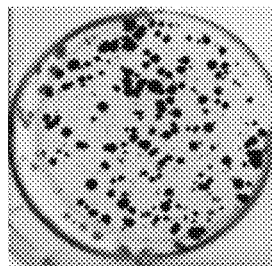
Figure 3D:
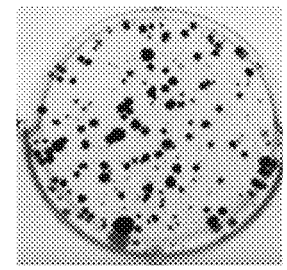
Figure 3E:
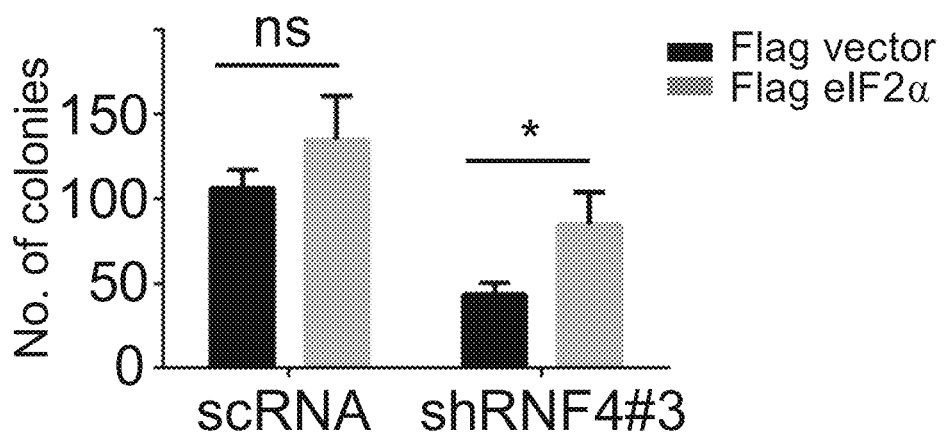
Figure 3F:
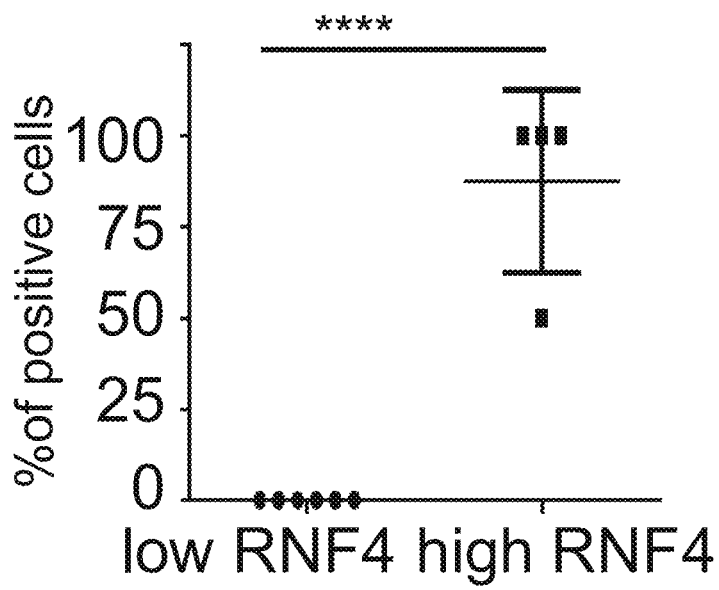
Figure 3G:
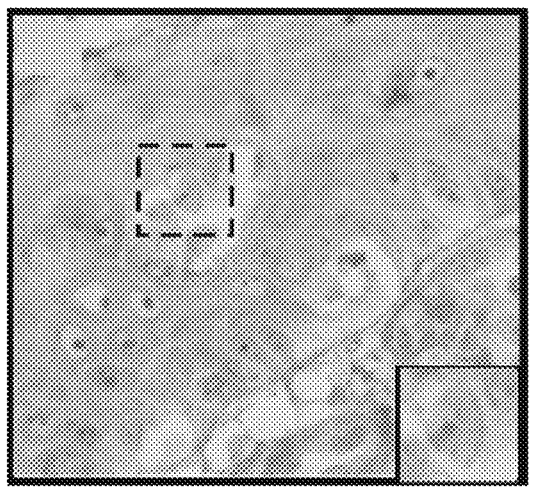
Figure 3H:
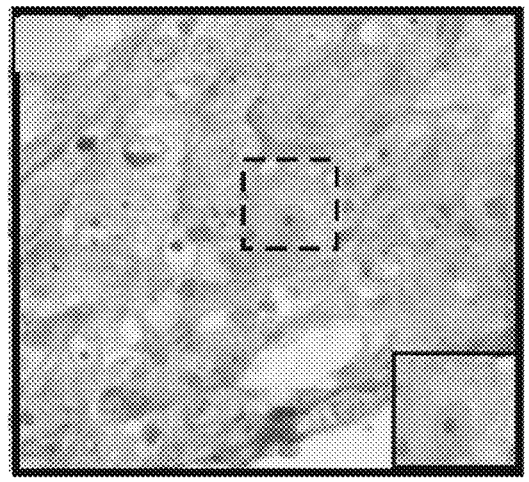
Figure 3I:
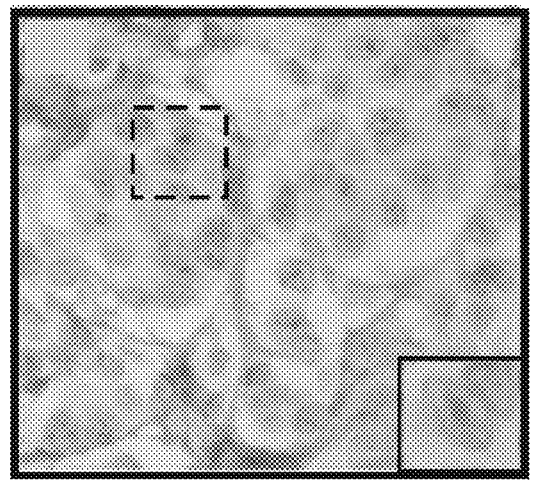
Figure 3J:
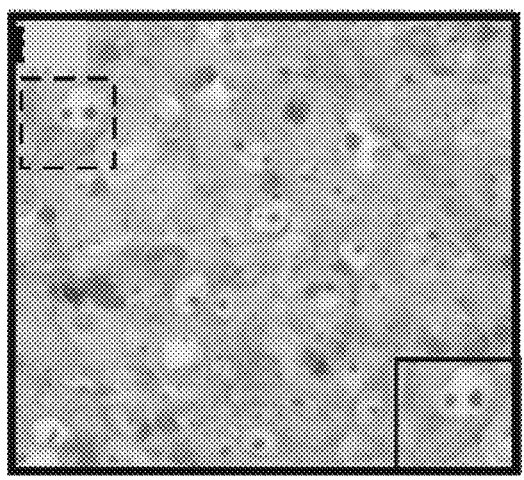
Figure 3K:
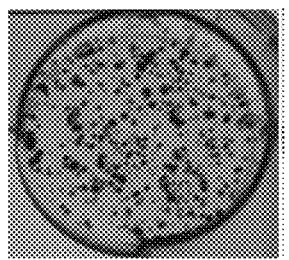
Figure 3L:
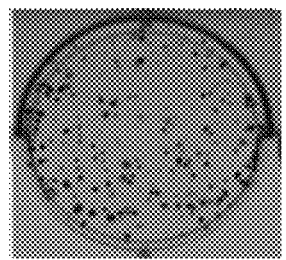
Figure 3M:
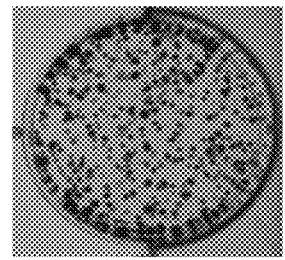
Figure 3N:
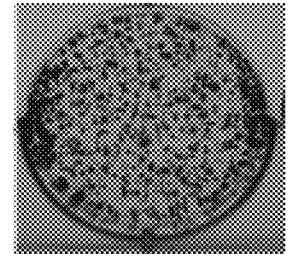
Figure 3O:
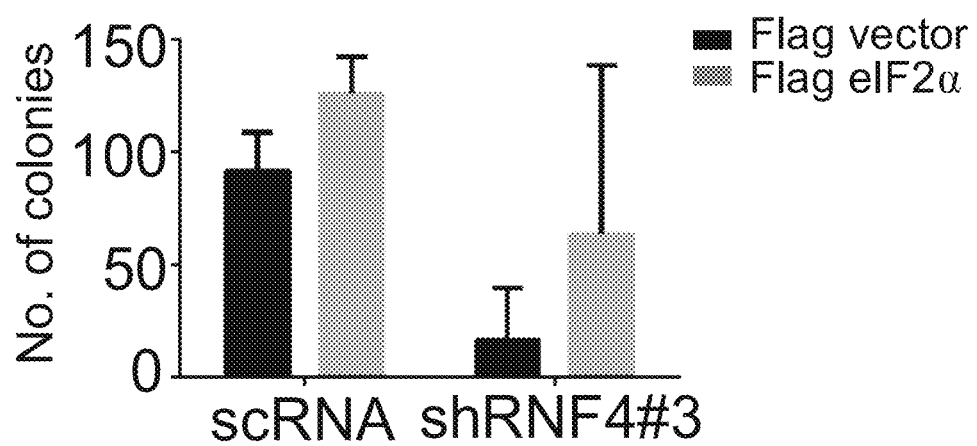

Analyzing patient-derived melanoma TMA, the inventors found that ~28.5% (6/21) of melanomas derived from non-responder patients to Paclitaxel-Sorafenib-Carboplatin-treatment melanomas expressed a high level of RNF4 protein, as detected using the anti-RNF4 antibody (FIG. 2A). Moreover, all (100%) biopsies with high level of RNF4 were resistant to this therapy. In contrast, all responsive melanomas expressed low RNF4 protein levels (n=10). Indeed, complementing this observation the inventors found that targeting Vemurafenib-resistant A375R melanoma cells by shRNF4 but not scRNA (control) re-sensitized A375R to Vemurafenib (FIG. 2B). Likewise, in a A375Rcells xenograft mouse model, targeting RNF4 in the presence of Vemurafenib attenuated tumor growth in the presence of the drug (FIG. 2C).

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. An antibody or antigen-binding portion thereof having specific binding affinity to RING finger protein 4 (RNF4), the antibody or antigen-binding portion thereof comprising three light chain CDRs ($V_L$CDR) and three heavy chain CDRs ($V_H$CDR), wherein:
- $V_{L1}$ CDR comprises the amino acid sequence as set forth in SEQ ID NO: 1 (SASSSVSYMY),
- $V_{L2}$ CDR comprises the amino acid sequence as set forth in SEQ ID NO: 2 (LTSNLAS),
- $V_{L3}$ CDR comprises the amino acid sequence as set forth in SEQ ID NO: 3 (QQWSSNPYM),
- $V_{H1}$ CDR comprises the amino acid sequence as set forth in SEQ ID NO: 4 (SYVMH),
- $V_{H2}$ CDR comprises the amino acid sequence as set forth in SEQ ID NO: 5 (YINPNNDGTKYNEKFKG), and
- $V_{H3}$ CDR comprises the amino acid sequence as set forth in SEQ ID NO: 6 (RVGHY).

2. The antibody or an antigen-binding portion thereof of claim 1, comprising a variable region light chain comprising the amino acid sequence of SEQ ID NO: 7.

3. The antibody or an antigen-binding portion thereof of claim 1, comprising a variable region heavy chain comprising the amino acid sequence of SEQ ID NO: 8.

4. The antibody or an antigen-binding portion thereof of claim 1, comprising a constant region light chain comprising the amino acid sequence of SEQ ID NO: 9.

5. The antibody or an antigen-binding portion thereof of claim 1, comprising a constant region heavy chain comprising the amino acid sequence of SEQ ID NO: 10.

6. The antibody or an antigen-binding portion thereof of claim 1, comprising a light chain comprising the amino acid sequence of SEQ ID NO: 11.

7. The antibody or an antigen-binding portion thereof of claim 1, comprising a heavy chain comprising the amino acid sequence of SEQ ID NO: 12.

8. The antibody or an antigen-binding portion thereof of claim 1, wherein the antigen binding fragment is selected from the group consisting of a Fv, Fab, F(ab')2, scFv or a scFv$_2$ fragment.

9. A composition comprising the antibody or an antigen-binding portion thereof of claim 1, and an acceptable carrier.

10. A method of detecting increased RNF4 levels in a sample compared to a baseline, comprising a step of contacting a sample with a first antibody, wherein said first antibody is the antibody or an antigen-binding portion thereof of claim 1, and detecting increased binding between the RNF4 and said first antibody compared to said baseline, thereby detecting increased RNF4 levels in the sample.

11. The method of claim 10, further comprising a step of contacting said sample with a second antibody or an antigen-binding portion thereof having specific binding affinity for phosphorylated translation initiation factor 2α (p-IF2α), and detecting increased binding between the p-IF2α and said second antibody in the sample compared to said baseline.

12. The method of claim 11, wherein said sample is derived from a subject.

13. The method of claim 12, wherein any one of: (i) increased binding between the RNF4 and said first antibody in said sample is indicative of said subject being afflicted with a RNF4-associated disease; (ii) increased binding between the RNF4 and said first antibody in said sample is indicative of said subject having poor RNF4-associated disease prognosis, and (iii) increased binding between the p-IF2α and said second antibody in the sample compared to said baseline is indicative of: said subject being afflicted with a RNF4-associated disease, said subject having poor RNF4-associated disease prognosis, or both.

14. The method of claim 12, further comprising a step of administering to said subject a therapeutically effective amount of an immune checkpoint inhibitor or a pharmaceutical composition comprising thereof.

15. The method of claim 14, wherein said immune checkpoint inhibitor is selected from the group consisting of: Pembrolizumab, Ipilimumab, Nivolumab, Atezolimumab, Avelumab, Durvalumab, and Cemiplimab.

16. The method of claim 12, wherein said RNF4-associated disease is cancer.

17. The method of claim 16, wherein said cancer is Estrogen Receptor α negative type of cancer ($ER_α$-negative).

18. A kit for detecting increased RNF4 levels in a sample, comprising:
   a. a first antibody, wherein the first antibody is the antibody or an antigen-binding portion thereof of claim 1; and
   b. a polynucleotide complementary to RNF4.

19. The kit of claim 18, comprising any one of: (i) a second antibody or an antigen-binding portion thereof having specific binding affinity to p-IF2α; and (ii) instructions for:
   a. contacting said sample with said antibody or an antigen-binding portion thereof, or with said polynucleotide complementary to RNF4; and
   b. detecting increased binding of the RNF4 with said antibody or with said complementary polynucleotide, compared to a baseline, thereby detecting increased RNF4 levels in the sample.

* * * * *

SEQUENCE LISTING

```
<160> NUMBER OF SEQ ID NOS: 25

<210> SEQ ID NO 1
<211> LENGTH: 10
<212> TYPE: PRT
<213> ORGANISM: Homo sapiens

<400> SEQUENCE: 1

Ser Ala Ser Ser Ser Val Ser Tyr Met Tyr
1               5                   10

<210> SEQ ID NO 2
<211> LENGTH: 7
<212> TYPE: PRT
<213> ORGANISM: Homo sapiens

<400> SEQUENCE: 2

Leu Thr Ser Asn Leu Ala Ser
1               5

<210> SEQ ID NO 3
<211> LENGTH: 9
<212> TYPE: PRT
<213> ORGANISM: Homo sapiens

<400> SEQUENCE: 3

Gln Gln Trp Ser Ser Asn Pro Tyr Met
1               5

<210> SEQ ID NO 4
```

```
<211> LENGTH: 5
<212> TYPE: PRT
<213> ORGANISM: Homo sapiens

<400> SEQUENCE: 4

Ser Tyr Val Met His
1               5

<210> SEQ ID NO 5
<211> LENGTH: 17
<212> TYPE: PRT
<213> ORGANISM: Homo sapiens

<400> SEQUENCE: 5

Tyr Ile Asn Pro Asn Asn Asp Gly Thr Lys Tyr Asn Glu Lys Phe Lys
1               5                   10                  15

Gly

<210> SEQ ID NO 6
<211> LENGTH: 5
<212> TYPE: PRT
<213> ORGANISM: Homo sapiens

<400> SEQUENCE: 6

Arg Val Gly His Tyr
1               5

<210> SEQ ID NO 7
<211> LENGTH: 128
<212> TYPE: PRT
<213> ORGANISM: Homo sapiens

<400> SEQUENCE: 7

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
                20                  25                  30

Met Ser Ala Ser Pro Gly Glu Lys Val Thr Met Thr Cys Ser Ala Ser
            35                  40                  45

Ser Ser Val Ser Tyr Met Tyr Trp Tyr Gln Gln Lys Pro Arg Ser Ser
        50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Tyr Met Phe Gly Gly Gly Thr Lys Leu Glu Ile Lys
        115                 120                 125

<210> SEQ ID NO 8
<211> LENGTH: 133
<212> TYPE: PRT
<213> ORGANISM: Homo sapiens

<400> SEQUENCE: 8

Met Glu Trp Ser Trp Ile Phe Leu Phe Leu Leu Ser Gly Thr Ala Gly
1               5                   10                  15

Val His Ser Glu Val Gln Leu Gln Gln Ser Arg Pro Gly Leu Val Lys
                20                  25                  30
```

Pro Gly Ala Ser Val Lys Met Ser Cys Lys Ala Ser Gly Tyr Thr Phe
            35                  40                  45

Thr Ser Tyr Val Met His Trp Val Lys Gln Lys Pro Gly Gln Gly Leu
 50                  55                  60

Glu Trp Ile Gly Tyr Ile Asn Pro Asn Asn Asp Gly Thr Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Asp Leu Ser Ser Leu Thr Ser Glu Asp Ser Ala Val
                100                 105                 110

Tyr Tyr Cys Ala Ser Arg Val Gly His Tyr Trp Gly Gln Gly Thr Ser
            115                 120                 125

Val Thr Val Ser Ser
        130

<210> SEQ ID NO 9
<211> LENGTH: 107
<212> TYPE: PRT
<213> ORGANISM: Homo sapiens

<400> SEQUENCE: 9

Arg Ala Asp Ala Ala Pro Thr Val Ser Ile Phe Pro Pro Ser Ser Glu
 1               5                  10                  15

Gln Leu Thr Ser Gly Gly Ala Ser Val Val Cys Phe Leu Asn Asn Phe
                20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
 50                  55                  60

Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 10
<211> LENGTH: 330
<212> TYPE: PRT
<213> ORGANISM: Homo sapiens

<400> SEQUENCE: 10

Ala Lys Thr Thr Ala Pro Ser Val Tyr Pro Leu Ala Pro Val Cys Gly
 1               5                  10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
 50                  55                  60

Ser Ser Ser Val Thr Val Thr Ser Ser Thr Trp Pro Ser Gln Ser Ile
 65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

-continued

Pro Ala Pro Asn Leu Leu Gly Gly Pro Ser Val Phe Ile Phe Pro Pro
115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 11
<211> LENGTH: 235
<212> TYPE: PRT
<213> ORGANISM: Homo sapiens

<400> SEQUENCE: 11

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Ser Val Ser Tyr Met Tyr Trp Tyr Gln Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Tyr Met Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

```
Tyr Pro Lys Asp Ile Asn Val Lys Trp Lys Ile Asp Gly Ser Glu Arg
            165                 170                 175

Gln Asn Gly Val Leu Asn Ser Trp Thr Asp Gln Asp Ser Lys Asp Ser
        180                 185                 190

Thr Tyr Ser Met Ser Ser Thr Leu Thr Leu Thr Lys Asp Glu Tyr Glu
    195                 200                 205

Arg His Asn Ser Tyr Thr Cys Glu Ala Thr His Lys Thr Ser Thr Ser
210                 215                 220

Pro Ile Val Lys Ser Phe Asn Arg Asn Glu Cys
225                 230                 235

<210> SEQ ID NO 12
<211> LENGTH: 463
<212> TYPE: PRT
<213> ORGANISM: Homo sapiens

<400> SEQUENCE: 12

Met Glu Trp Ser Trp Ile Phe Leu Phe Leu Leu Ser Gly Thr Ala Gly
1               5                   10                  15

Val His Ser Glu Val Gln Leu Gln Gln Ser Arg Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Asn Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Asp Leu Ser Ser Leu Thr Ser Glu Asp Ser Ala Val
            100                 105                 110

Tyr Tyr Cys Ala Ser Arg Val Gly His Tyr Trp Gly Gln Gly Thr Ser
        115                 120                 125

Val Thr Val Ser Ser Ala Lys Thr Thr Ala Pro Ser Val Tyr Pro Leu
130                 135                 140

Ala Pro Val Cys Gly Asp Thr Thr Gly Ser Ser Val Thr Leu Gly Cys
145                 150                 155                 160

Leu Val Lys Gly Tyr Phe Pro Glu Pro Val Thr Leu Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Ser Val Thr Val Thr Ser Ser Thr Trp
        195                 200                 205

Pro Ser Gln Ser Ile Thr Cys Asn Val Ala His Pro Ala Ser Ser Thr
210                 215                 220

Lys Val Asp Lys Lys Ile Glu Pro Arg Gly Pro Thr Ile Lys Pro Cys
225                 230                 235                 240

Pro Pro Cys Lys Cys Pro Ala Pro Asn Leu Leu Gly Gly Pro Ser Val
                245                 250                 255

Phe Ile Phe Pro Pro Lys Ile Lys Asp Val Leu Met Ile Ser Leu Ser
            260                 265                 270

Pro Ile Val Thr Cys Val Val Asp Val Ser Glu Asp Asp Pro Asp
        275                 280                 285

Val Gln Ile Ser Trp Phe Val Asn Asn Val Glu Val His Thr Ala Gln
```

```
                290                 295                 300
Thr Gln Thr His Arg Glu Asp Tyr Asn Ser Thr Leu Arg Val Val Ser
305                 310                 315                 320

Ala Leu Pro Ile Gln His Gln Asp Trp Met Ser Gly Lys Glu Phe Lys
                325                 330                 335

Cys Lys Val Asn Asn Lys Asp Leu Pro Ala Pro Ile Glu Arg Thr Ile
                340                 345                 350

Ser Lys Pro Lys Gly Ser Val Arg Ala Pro Gln Val Tyr Val Leu Pro
                355                 360                 365

Pro Pro Glu Glu Glu Met Thr Lys Lys Gln Val Thr Leu Thr Cys Met
370                 375                 380

Val Thr Asp Phe Met Pro Glu Asp Ile Tyr Val Glu Trp Thr Asn Asn
385                 390                 395                 400

Gly Lys Thr Glu Leu Asn Tyr Lys Asn Thr Glu Pro Val Leu Asp Ser
                405                 410                 415

Asp Gly Ser Tyr Phe Met Tyr Ser Lys Leu Arg Val Glu Lys Lys Asn
                420                 425                 430

Trp Val Glu Arg Asn Ser Tyr Ser Cys Ser Val Val His Glu Gly Leu
                435                 440                 445

His Asn His His Thr Thr Lys Ser Phe Ser Arg Thr Pro Gly Lys
                450                 455                 460

<210> SEQ ID NO 13
<211> LENGTH: 30
<212> TYPE: DNA
<213> ORGANISM: Homo sapiens

<400> SEQUENCE: 13
agtgccagtt caagtgtaag ttacatgtac                                          30

<210> SEQ ID NO 14
<211> LENGTH: 21
<212> TYPE: DNA
<213> ORGANISM: Homo sapiens

<400> SEQUENCE: 14
ctcacatcca acctggcttc t                                                   21

<210> SEQ ID NO 15
<211> LENGTH: 27
<212> TYPE: DNA
<213> ORGANISM: Homo sapiens

<400> SEQUENCE: 15
cagcagtgga gtagtaaccc gtacatg                                             27

<210> SEQ ID NO 16
<211> LENGTH: 384
<212> TYPE: DNA
<213> ORGANISM: Homo sapiens

<400> SEQUENCE: 16
atggattttc aagtgcagat tttcagcttc ctgctaatga gtgcctcagt cataatgtcc         60
aggggacaaa ttgttctcac ccagtctcca gcactcatgt ctgcatctcc aggggagaag       120
gtcaccatga cctgcagtgc cagttcaagt gtaagttaca tgtactggta ccagcagaag       180
ccaagatctt cccccaaacc ctggatttat ctcacatcca acctggcttc tggagtccct       240
gctcgcttca gtggcagtgg gtctgggacc tcttactctc tcacaatcag cagcatggag       300
```

```
gctgaagatg ctgccactta ttactgccag cagtggagta gtaacccgta catgttcgga    360 gggggggacca agctggaaat aaaa                                          384

<210> SEQ ID NO 17
<211> LENGTH: 15
<212> TYPE: DNA
<213> ORGANISM: Homo sapiens

<400> SEQUENCE: 17
agctatgtta tgcac                                                     15

<210> SEQ ID NO 18
<211> LENGTH: 51
<212> TYPE: DNA
<213> ORGANISM: Homo sapiens

<400> SEQUENCE: 18
tatattaatc ctaacaatga cggtactaag tacaatgaga agttcaaagg c             51

<210> SEQ ID NO 19
<211> LENGTH: 15
<212> TYPE: DNA
<213> ORGANISM: Homo sapiens

<400> SEQUENCE: 19
cgggtcgggc actac                                                     15

<210> SEQ ID NO 20
<211> LENGTH: 399
<212> TYPE: DNA
<213> ORGANISM: Homo sapiens

<400> SEQUENCE: 20
atggaatgga gttggatatt tctctttctc ctgtcaggaa ctgcaggtgt ccactctgag    60
gtccagctgc agcagtctcg acctgagctg gtaaagcctg ggcttcagt gaagatgtcc    120 tgcaaggctt ctggatacac attcactagc tatgttatgc actgggtgaa gcagaagcct    180
gggcagggcc ttgagtggat tggatatatt aatcctaaca atgacggtac taagtacaat    240
gagaagttca aaggcaaggc cacactgact tcagacaaat cctccagcac agcctatatg    300
gacctcagca gcctgacctc tgaggactct gcggtctatt actgtgcaag ccgggtcggg    360
cactactggg gtcaaggaac ctcagtcacc gtctcctca                           399

<210> SEQ ID NO 21
<211> LENGTH: 324
<212> TYPE: DNA
<213> ORGANISM: Homo sapiens

<400> SEQUENCE: 21
cgggctgatg ctgcaccaac tgtatccatc ttcccaccat ccagtgagca gttaacatct    60
ggaggtgcct cagtcgtgtg cttcttgaac aacttctacc ccaaagacat caatgtcaag    120
tggaagattg atggcagtga acgacaaaat ggcgtcctga cagttggac tgatcaggac    180 agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg ttag                                           324

<210> SEQ ID NO 22
```

```
<211> LENGTH: 993
<212> TYPE: DNA
<213> ORGANISM: Homo sapiens

<400> SEQUENCE: 22
gccaaaacaa cagccccatc ggtctatcca ctggcccctg tgtgtggaga tacaactggc      60
tcctcggtga ctctaggatg cctggtcaag ggttatttcc ctgagccagt gaccttgacc     120
tggaactctg gatccctgtc cagtggtgtg cacaccttcc cagctgtcct gcagtctgac     180
ctctacaccc tcagcagctc agtgactgta acctcgagca cctggcccag ccagtccatc     240
acctgcaatg tgcccacccc ggcaagcagc accaaggtgg acaagaaaat tgagcccaga     300
gggcccacaa tcaagccctg tcctccatgc aaatgcccag cacctaacct cttgggtgga     360
ccatccgtct tcatcttccc tccaaagatc aaggatgtac tcatgatctc cctgagcccc     420
atagtcacat gtgtggtggt ggatgtgagc gaggatgacc cagatgtcca gatcagctgg     480
tttgtgaaca acgtggaagt acacacagct cagacacaaa cccatagaga ggattacaac     540
agtactctcc gggtggtcag tgccctcccc atccagcacc aggactggat gagtggcaag     600
gagttcaaat gcaaggtcaa caacaaagac ctcccagcgc ccatcgagag aaccatctca     660
aaacccaaag ggtcagtaag agctccacag gtatatgtct tgcctccacc agaagaagag     720
atgactaaga acaggtcac tctgacctgc atggtcacag acttcatgcc tgaagacatt     780
tacgtggagt ggaccaacaa cgggaaaaca gagctaaact acaagaacac tgaaccagtc     840
ctggactctg atggttctta cttcatgtac agcaagctga gagtggaaaa gaagaactgg     900
gtggaaagaa atagcactc ctgttcagtg gtccacgagg gtctgcacaa tcaccacacg     960
actaagagct ctcccggac tccgggtaaa tga                                   993

<210> SEQ ID NO 23
<211> LENGTH: 708
<212> TYPE: DNA
<213> ORGANISM: Homo sapiens

<400> SEQUENCE: 23
atggattttc aagtgcagat tttcagcttc ctgctaatga gtgcctcagt cataatgtcc      60
aggggacaaa ttgttctcac ccagtctcca gcactcatgt ctgcatctcc aggggagaag     120
gtcaccatga cctgcagtgc cagttcaagt gtaagttaca tgtactggta ccagcagaag     180
ccaagatctt cccccaaacc ctggatttat ctcacatcca acctggcttc tggagtccct     240
gctcgcttca gtggcagtgg gtctgggacc tcttactctc tcacaatcag cagcatggag     300
gctgaagatg ctgccactta ttactgccag cagtggagta gtaacccgta catgttcgga     360 gggggggacca agctggaaat aaaacgggct gatgctgcac caactgtatc catcttccca     420
ccatccagtg agcagttaac atctggaggt gcctcagtcg tgtgcttctt gaacaacttc     480
taccccaaag acatcaatgt caagtggaag attgatggca gtgaacgaca aaatggcgtc     540
ctgaacagtt ggactgatca ggacagcaaa gacagcacct acagcatgag cagcacccct     600
acgttgacca aggacgagta tgaacgacat aacagctata cctgtgaggc cactcacaag     660
acatcaactt cacccattgt caagagcttc aacaggaatg agtgttag                  708

<210> SEQ ID NO 24
<211> LENGTH: 1392
<212> TYPE: DNA
<213> ORGANISM: Homo sapiens

<400> SEQUENCE: 24
```

```
atggaatgga gttggatatt tctctttctc ctgtcaggaa ctgcaggtgt ccactctgag     60
gtccagctgc agcagtctcg acctgagctg gtaaagcctg gggcttcagt gaagatgtcc    120
tgcaaggctt ctggatacac attcactagc tatgttatgc actgggtgaa gcagaagcct    180
gggcagggcc ttgagtggat tggatatatt aatcctaaca atgacggtac taagtacaat    240
gagaagttca aggcaaggc cacactgact tcagacaaat cctccagcac agcctatatg     300
gacctcagca gcctgacctc tgaggactct gcggtctatt actgtgcaag ccgggtcggg    360
cactactggg gtcaaggaac ctcagtcacc gtctcctcag ccaaaacaac agccccatcg    420
gtctatccac tggcccctgt gtgtggagat acaactggct cctcggtgac tctaggatgc    480
ctggtcaagg gttatttccc tgagccagtg accttgacct ggaactctgg atccctgtcc    540
agtggtgtgc acaccttccc agctgtcctg cagtctgacc tctacaccct cagcagctca    600
gtgactgtaa cctcgagcac ctggcccagc cagtccatca cctgcaatgt ggcccacccg    660
gcaagcagca ccaaggtgga caagaaaatt gagcccagag ggcccacaat caagccctgt    720
cctccatgca aatgcccagc acctaacctc ttgggtggac catccgtctt catcttccct    780
ccaaagatca aggatgtact catgatctcc ctgagcccca tagtcacatg tgtggtggtg    840
gatgtgagcg aggatgaccc agatgtccag atcagctggt ttgtgaacaa cgtggaagta    900
cacacagctc agacacaaac ccatagagag gattacaaca gtactctccg ggtggtcagt    960
gccctcccca tccagcacca ggactggatg agtggcaagg agttcaaatg caaggtcaac   1020
aacaaagacc tcccagcgcc catcgagaga accatctcaa acccaaagg gtcagtaaga   1080
gctccacagg tatatgtctt gcctccacca gaagaagaga tgactaagaa acaggtcact   1140
ctgacctgca tggtcacaga cttcatgcct gaagacattt acgtggagtg gaccaacaac   1200
gggaaaacag agctaaacta caagaacact gaaccagtcc tggactctga tggttcttac   1260
ttcatgtaca gcaagctgag agtggaaaag aagaactggg tggaaagaaa tagctactcc   1320
tgttcagtgg tccacgaggg tctgcacaat caccacacga ctaagagctt ctcccggact   1380
ccgggtaaat ga                                                        1392
```

<210> SEQ ID NO 25
<211> LENGTH: 190
<212> TYPE: PRT
<213> ORGANISM: Homo sapiens

<400> SEQUENCE: 25

```
Met Ser Thr Arg Lys Arg Arg Gly Gly Ala Ile Asn Ser Arg Gln Ala
1               5                   10                  15

Gln Lys Arg Thr Arg Glu Ala Thr Ser Thr Pro Glu Ile Ser Leu Glu
            20                  25                  30

Ala Glu Pro Ile Glu Leu Val Glu Thr Ala Gly Asp Glu Ile Val Asp
        35                  40                  45

Leu Thr Cys Glu Ser Leu Glu Pro Val Val Asp Leu Thr His Asn
    50                  55                  60

Asp Ser Val Val Ile Val Asp Glu Arg Arg Pro Arg Arg Asn Ala
65                  70                  75                  80

Arg Arg Leu Pro Gln Asp His Ala Asp Ser Cys Val Val Ser Ser Asp
            85                  90                  95

Asp Glu Glu Leu Ser Arg Asp Arg Asp Val Tyr Val Thr Thr His Thr
            100                 105                 110

Pro Arg Asn Ala Arg Asp Glu Gly Ala Thr Gly Leu Arg Pro Ser Gly
```

```
            115                 120                 125
Thr Val Ser Cys Pro Ile Cys Met Asp Gly Tyr Ser Glu Ile Val Gln
        130                 135                 140

Asn Gly Arg Leu Ile Val Ser Thr Glu Cys Gly His Val Phe Cys Ser
145                 150                 155                 160

Gln Cys Leu Arg Asp Ser Leu Lys Asn Ala Asn Thr Cys Pro Thr Cys
                165                 170                 175

Arg Lys Lys Ile Asn His Lys Arg Tyr His Pro Ile Tyr Ile
                180                 185                 190
```